(12) United States Patent
Besser et al.

(10) Patent No.: US 8,827,951 B2
(45) Date of Patent: Sep. 9, 2014

(54) BALLOON CATHETER SYSTEM AND METHODS OF USE THEREOF

(76) Inventors: Doron Besser, Tel Aviv (IL); Eran Harari, Maagan Michael (IL)

(*) Notice: Subject to any disclaimer, the term of this patent is extended or adjusted under 35 U.S.C. 154(b) by 177 days.

(21) Appl. No.: 13/001,433

(22) PCT Filed: Jul. 2, 2009

(86) PCT No.: PCT/IL2009/000667
§ 371 (c)(1),
(2), (4) Date: Aug. 1, 2011

(87) PCT Pub. No.: WO2010/001404
PCT Pub. Date: Jan. 7, 2010

(65) Prior Publication Data
US 2011/0275990 A1    Nov. 10, 2011

Related U.S. Application Data

(60) Provisional application No. 61/077,496, filed on Jul. 2, 2008, provisional application No. 61/077,520, filed on Jul. 2, 2008, provisional application No. 61/143,847, filed on Jan. 12, 2009.

(51) Int. Cl.
*A61M 29/00* (2006.01)

(52) U.S. Cl.
USPC ...................................... 604/97.02

(58) Field of Classification Search
USPC .......... 604/96.01, 97.01, 97.02, 97.03, 98.01, 604/99.01
See application file for complete search history.

(56) References Cited

U.S. PATENT DOCUMENTS

| 4,004,588 A | 1/1977 | Alexander |
| 4,243,040 A | 1/1981 | Beecher |
| 4,271,839 A | 6/1981 | Fogarty et al. |
| 4,469,100 A | 9/1984 | Hardwick |
| 4,597,389 A | 7/1986 | Ibrahim |
| 4,611,594 A | 9/1986 | Grayhack et al. |
| 4,748,982 A | 6/1988 | Horzewski |
| 4,762,129 A | 8/1988 | Bonzel |
| 4,946,440 A | 8/1990 | Hall |

(Continued)

FOREIGN PATENT DOCUMENTS

| CA | 2183214 | 2/1998 |
| EP | 0200668 | 12/1986 |

(Continued)

*Primary Examiner* — Nicholas D Lucchesi
*Assistant Examiner* — Pritesh Patel
(74) *Attorney, Agent, or Firm* — Daniel J. Swirsky; AlphaPatent Associates Ltd.

(57) ABSTRACT

A catheter including an outer conduit and an inner conduit movably disposed therein. The distal tip of the inner conduit extends beyond the distal tip of the outer conduit. An inflatable balloon has a first margin attached to the distal tip of the outer conduit, and a second margin attached to the portion of the inner conduit extending beyond the distal tip of the outer conduit. The balloon includes a middle portion, an inflatable distal side portion having at least one tapering part and an inflatable proximal side portion having at least one tapering portion. The length of proximal side portion is equal to or larger than the length of the middle portion. The distal end portion of the balloon is capable of intussuscepting upon proximal movement of the inner conduit within the outer conduit. The catheter includes an inflation/deflation port for introducing and removal of inflating fluid.

27 Claims, 9 Drawing Sheets

(56) References Cited

U.S. PATENT DOCUMENTS

| | | |
|---|---|---|
| 4,955,895 A | 9/1990 | Sugiyama et al. |
| 5,019,041 A | 5/1991 | Robinson et al. |
| 5,092,839 A | 3/1992 | Kipperman |
| 5,109,830 A | 5/1992 | Cho |
| 5,254,091 A | 10/1993 | Aliahmad et al. |
| 5,307,814 A | 5/1994 | Kressel et al. |
| RE34,633 E | 6/1994 | Sos et al. |
| 5,338,298 A | 8/1994 | McIntyre |
| 5,437,638 A | 8/1995 | Bowman |
| 5,470,314 A | 11/1995 | Walinsky |
| 5,534,007 A | 7/1996 | St. Germain et al. |
| 5,630,822 A | 5/1997 | Hermann et al. |
| 5,785,675 A | 7/1998 | Drasler et al. |
| 5,865,801 A | 2/1999 | Houser |
| 5,868,767 A | 2/1999 | Farley et al. |
| 5,941,895 A | 8/1999 | Myler et al. |
| 6,004,341 A | 12/1999 | Zhu et al. |
| 6,022,359 A | 2/2000 | Frantzen |
| 6,039,721 A | 3/2000 | Johnson |
| 6,129,706 A | 10/2000 | Janacek |
| 6,152,947 A | 11/2000 | Ambrisco et al. |
| 6,179,827 B1 | 1/2001 | Davis et al. |
| 6,280,412 B1 | 8/2001 | Pederson, Jr. et al. |
| 6,383,195 B1 | 5/2002 | Richard |
| 6,695,810 B2 | 2/2004 | Peacock, III et al. |
| 7,201,770 B2 | 4/2007 | Johnson et al. |
| 7,591,831 B2 | 9/2009 | Parsonage et al. |
| 2002/0082639 A1 | 6/2002 | Broome et al. |
| 2002/0121472 A1 | 9/2002 | Garner et al. |
| 2002/0177870 A1 | 11/2002 | Sepetka et al. |
| 2003/0028211 A1 | 2/2003 | Crocker et al. |
| 2003/0055483 A1 | 3/2003 | Gumm |
| 2003/0105508 A1 | 6/2003 | Johnson et al. |
| 2003/0130672 A1 | 7/2003 | Dobrava et al. |
| 2003/0176884 A1 | 9/2003 | Berrada et al. |
| 2003/0176910 A1 | 9/2003 | Vrba et al. |
| 2003/0208223 A1 | 11/2003 | Kleiner |
| 2004/0054362 A1 | 3/2004 | Lopath et al. |
| 2004/0073243 A1 | 4/2004 | Sepetka et al. |
| 2004/0236275 A1 | 11/2004 | Pruitt et al. |
| 2004/0236367 A1 | 11/2004 | Brown et al. |
| 2005/0004553 A1 | 1/2005 | Douk |
| 2005/0085826 A1 | 4/2005 | Nair et al. |
| 2005/0101986 A1 | 5/2005 | Daniel et al. |
| 2005/0102019 A1 | 5/2005 | Yadin |
| 2005/0137501 A1 | 6/2005 | Euteneuer et al. |
| 2005/0137607 A1 | 6/2005 | Assell et al. |
| 2005/0154414 A1 | 7/2005 | Perreault et al. |
| 2005/0187570 A1 | 8/2005 | Nguyen et al. |
| 2005/0209629 A1 | 9/2005 | Kerr et al. |
| 2005/0261705 A1 | 11/2005 | Gist |
| 2005/0288700 A1 | 12/2005 | Chermoni |
| 2006/0025720 A1 | 2/2006 | Sawa et al. |
| 2006/0129107 A1 | 6/2006 | McArthur et al. |
| 2006/0129710 A1 | 6/2006 | O'Connor et al. |
| 2007/0083158 A1 | 4/2007 | Hirszovicz et al. |
| 2007/0088380 A1 | 4/2007 | Hirszowicz et al. |
| 2007/0255305 A1 | 11/2007 | McMichael et al. |
| 2009/0204069 A1* | 8/2009 | Hirszowicz et al. ..... 604/103.04 |

FOREIGN PATENT DOCUMENTS

| | | |
|---|---|---|
| EP | 359 489 A | 3/1990 |
| EP | 380873 | 8/1990 |
| EP | 0380873 | 8/1990 |
| EP | 0987045 | 3/2000 |
| EP | 1333778 | 8/2003 |
| EP | 1 062 966 | 9/2004 |
| EP | 1062966 | 9/2004 |
| GB | 2054385 | 2/1981 |
| JP | 54-066582 A | 5/1979 |
| JP | 2000005189 A | 1/2000 |
| WO | WO 84/01513 A | 4/1984 |
| WO | WO 98/29026 | 7/1998 |
| WO | WO 00/02613 | 1/2000 |
| WO | WO 00/27309 | 5/2000 |
| WO | WO 00 38776 | 7/2000 |
| WO | WO 00/38776 | 7/2000 |
| WO | WO 02/38084 | 5/2002 |
| WO | WO 02/055146 | 7/2002 |
| WO | WO 2004/014240 | 2/2004 |
| WO | WO 2004/028611 | 4/2004 |
| WO | WO 2004/082462 | 9/2004 |
| WO | WO 2004/098681 | 11/2004 |
| WO | WO 2005/000130 | 1/2005 |
| WO | WO 2005/030308 | 4/2005 |
| WO | WO 2005/041788 | 5/2005 |
| WO | WO 2005/102184 | 11/2005 |
| WO | WO 2005/112783 | 12/2005 |
| WO | WO 2007/004221 | 1/2007 |
| WO | WO 2007/042935 | 4/2007 |
| WO | WO 2007/042936 | 4/2007 |
| WO | WO 2007/132464 | 11/2007 |
| WO | WO 2008/004238 | 1/2008 |
| WO | WO 2008/004239 | 1/2008 |

* cited by examiner

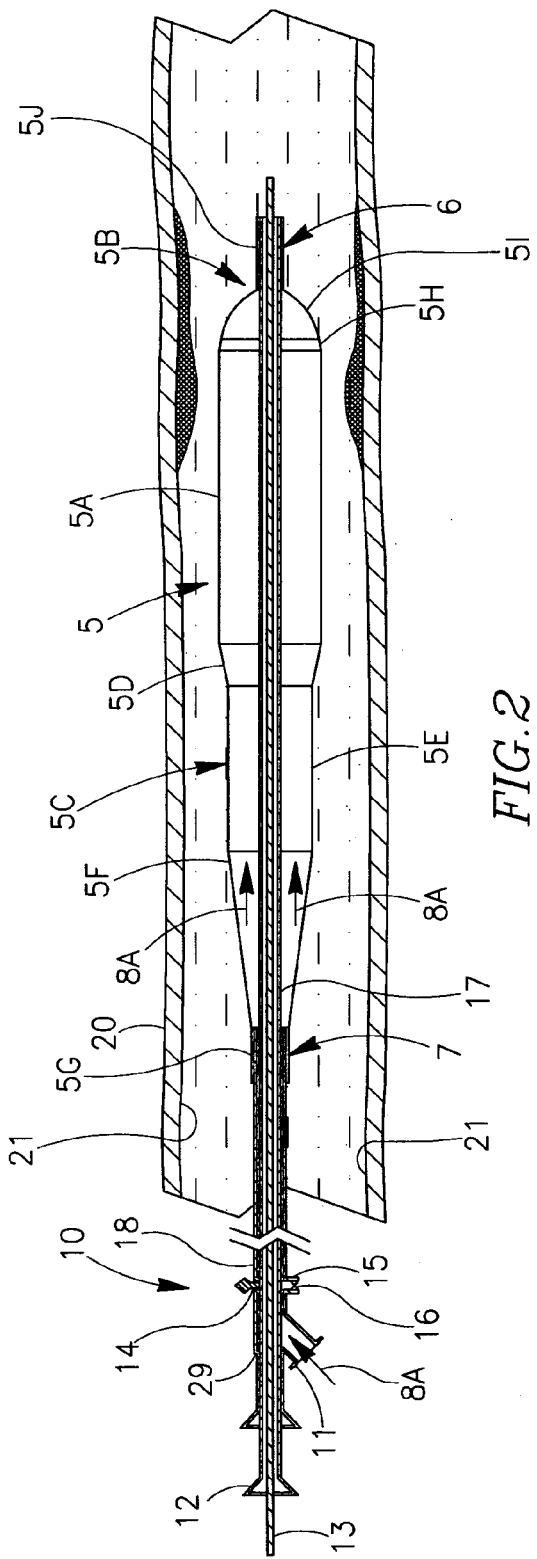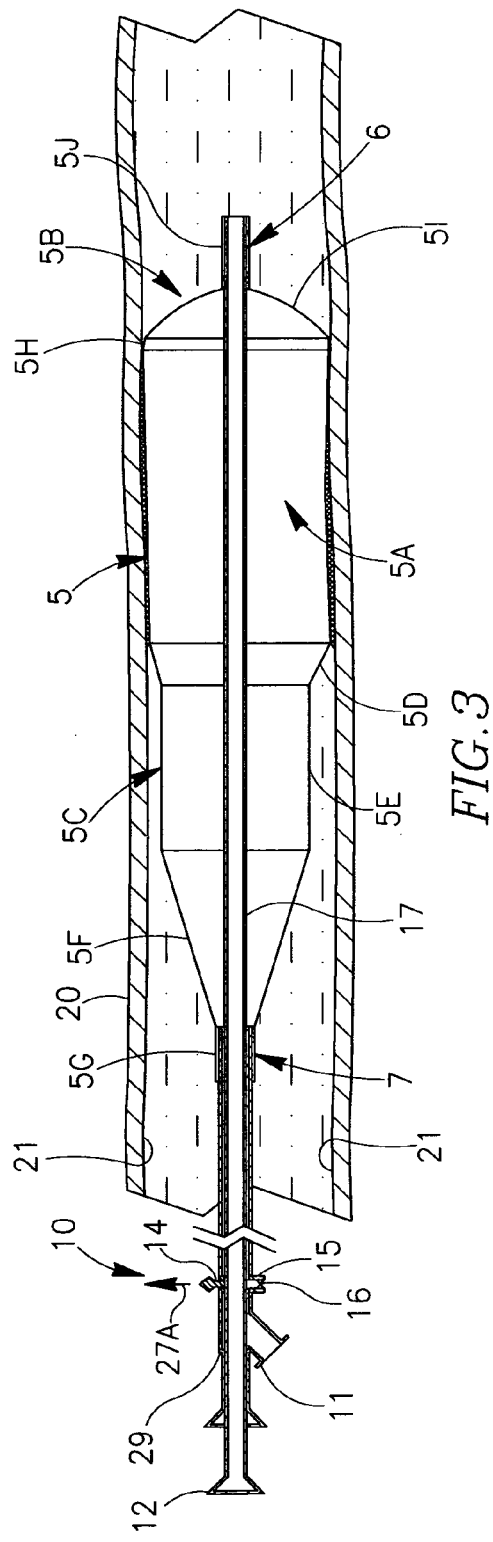

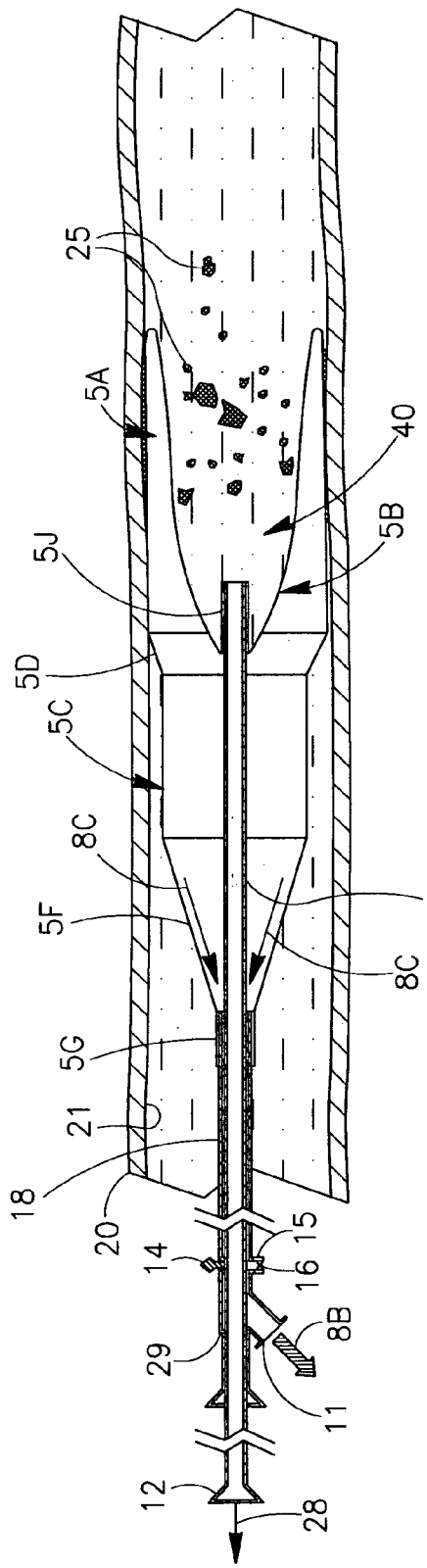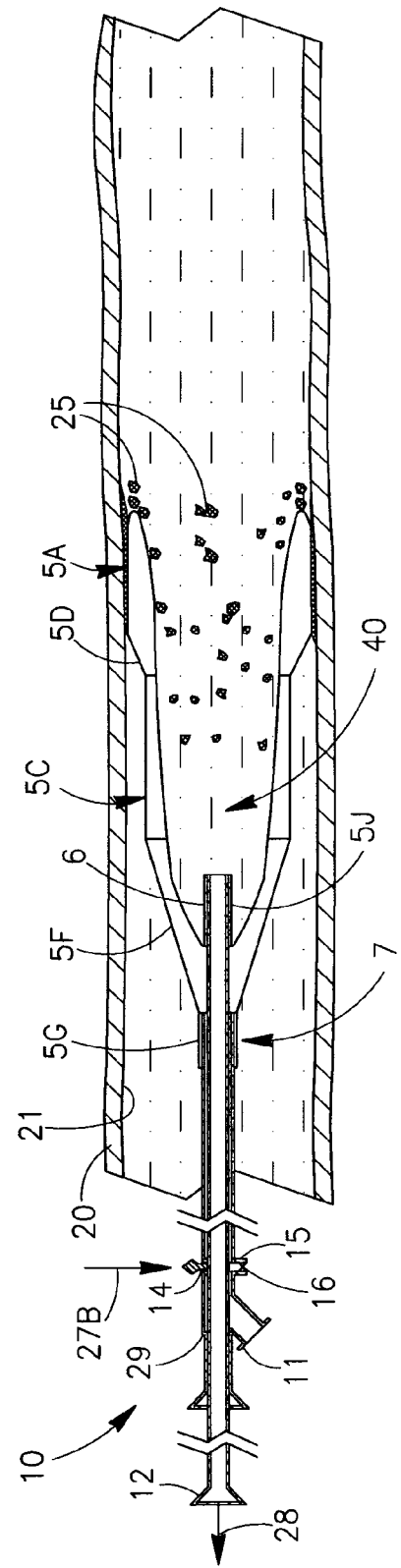
FIG. 4
FIG. 5

BALLOON CATHETER SYSTEM AND METHODS OF USE THEREOF

CROSS-REFERENCE TO RELATED APPLICATIONS

The current application is a U.S. National Phase Application under 35 U.S.C. 371 of PCT International Application No. PCT/IL2009/000667, which has an international filing date of Jul. 2, 2009, and which claims priority from and the benefit of U.S. Provisional Patent Application Ser. No. 61/077,496, filed on Jul. 2, 2008, titled "CORRUGATED BALLOON CATHETER SYSTEM AND METHODS OF USE THEREOF", U.S. Provisional Patent Application Ser. No. 61/077,520, filed on Jul. 2, 2008, titled 'CORRUGATED BALLOON CATHETER AND METHODS OF USE THEREOF", and U.S. Provisional Patent Application Ser. No. 61/143,847, filed on Jan. 12, 2009, titled "BALLOON AND CATHETER SYSTEM AND METHODS FOR MAKING SAME", all of which are incorporated herein by reference in their entirety.

FIELD OF THE INVENTION

This invention relates in general to the fields of medical balloon catheters and more particularly to catheters and systems having intussusceptible inflatable elements, systems including such catheters and methods of use and manufacturing of such catheters and systems.

BACKGROUND OF THE INVENTION

Catheters are used in various interventional procedures for delivering therapeutic means to a treated site (e.g., body organ or passageway such as blood vessels). In many cases, a catheter with a small distal inflatable balloon is guided to the treated site. Once the balloon is in place it is inflated by the operator for affixing it in place, for expanding a blocked vessel, for placing treatment means (e.g., stent) and/or for delivering surgical tools (e.g. knives, drills etc.) to a desired site. In addition, catheter systems have also been designed and used for retrieval of objects such as stents from body passageways.

Two basic types of catheter have been developed for intravascular use: over-the-wire (OTW) catheters and rapid-exchange catheters.

OTW catheter systems are characterized by the presence of a full-length guide wire, such that when the catheter is in its in situ working position, said guide wire passes through the entire length of a lumen formed in, or externally attached to, the catheter. OTW systems have several operational advantages which are related to the use of a full length guide wire, including good stiffness and pushability, features which are important when maneuvering balloon catheters along tortuous and/or partially occluded blood vessels.

U.S. Pat. No. 6,039,721 to Johnson et al., describes a balloon catheter system comprising two concentrically-arranged conduits, with a balloon connected between the distal regions thereof. The catheter system permits both expansion/deflation of the balloon and alteration in the length of the balloon when in situ, such that the balloon may be moved between extended and intussuscepted conformations. The catheter system is constructed in order that it may be used for two main purposes: firstly, treatment (i.e. expansion) of different-length stenosed portions of blood vessels with a single balloon and secondly, the delivery of either stents or medication to intravascular lesions, wherein the stent or medication is contained within the distally-intussuscepted portion of the balloon. When used for multiple, differing-length lesion expansion, the balloon is inserted into a blood vessel in a collapsed, shortened, intussuscepted conformation, and is advanced until it comes to rest in the region of the shortest lesion to be treated. The balloon is then inflated and the lesion treated (i.e. expanded). Following deflation of the balloon, the distal end of the catheter system is moved such that the balloon becomes positioned in the region of the next—shortest lesion to be treated. The effective length of the balloon is then increased by moving the inner conduit in relation to the proximal conduit, following which the balloon is again inflated and the lesion treated. In this way, a series of different length stenoses, in order from the shortest to the longest, may be treated using a single balloon. When used for stent delivery, the stent is pre-loaded into a proximal annular space formed as a result of balloon intussusception. The balloon is then moved to the desired site and the stent delivered by means of moving the inner conduit distally (in relation to the outer tube), thereby "unpeeling" the stent from the catheter.

WO 00/38776 discloses a dual-conduit balloon catheter system similar in basic design to that described above in relation to U.S. Pat. No. 6,039,721. This catheter system is intended for use in a vibratory mode in order to break through total occlusions of the vascular lumen. In order to fulfill this aim, the outer conduit has a variable stiffness along its length, while the inner conduit. In addition, the inner conduit while being intrinsically relatively flexible is stiffened by the presence of axial tensioning wires. These conduit design features are used in order to permit optimal translation of vibratory movements of the proximal end of the inner conduit into corresponding vibration of the distal tip thereof.

Rapid exchange ("monorail") catheters typically comprise a relatively short guide wire lumen provided in a distal section thereof, and a proximal guide wire exit port located between the catheter's distal and proximal ends. This arrangement allows exchange of the catheter over a relatively short guide wire, in a manner which is simple to perform and which can be carried out by a single operator. Rapid exchange catheters have been extensively described in the art, for example, U.S. Pat. Nos. 4,762,129, 4,748,982 and EP0380873.

Rapid exchange catheters are commonly used in Percutaneous Transluminal Coronary Angioplasty (PTCA) procedures, in which obstructed blood vessels are typically dilated by a distal balloon mounted on the catheter's distal end. A stent is often placed at the vessel's dilation zone to prevent reoccurrences of obstruction therein. The dilation balloon is typically inflated via an inflation lumen which extends longitudinally inside the catheter's shaft between the dilation balloon and the catheter's proximal end.

The guide wire lumen passes within a smaller section of the catheter's shaft length and it is accessed via a lateral port situated on the catheter's shaft. This arrangement, wherein the guidewire tube is affixed to the catheter's shaft at the location of its lateral port, usually prevents designers from developing new rapid exchange catheter implementations which requires manipulating its inner shaft. For example, extending or shortening the catheter's length during procedures may be advantageously exploited by physicians to distally extend the length of the catheter into a new site after or during its placement in the patient's artery, for example in order to assist with the passage of tortuous vessels or small diameter stenoses, or to allow in-situ manipulation of an inflated balloon at the distal end of the catheter.

Published International Patent Application, Publication No. WO 2005/102184 discloses a catheter having a rollable expandable element. Published International Patent applications, Publication Nos. WO 2007/004221, WO 2007/042935, WO 2008/004238 and WO 2008/004239, all five published international applications are incorporated herein by reference in their entirety for all purposes, disclose various types of catheters and catheter systems having intussuscepting balloon-like inflatable members which may be used, inter alia, to treat plaque by balloon inflation while efficiently collecting plaque debris and other particulate matter from the lumen of pathologically-involved blood vessels and to remove such particles and particulate matter from the blood vessel.

Such inflatable intususceptable balloons may be used to treat plaque by inflating and expanding the balloons after their placement in the plaque region of a blood vessel. Typically, the maximal outer diameter of the balloon in the fully inflated state is limited by the transversal size (or diameter) of the treated blood vessel. Therefore, if one desires to increase the volume available in the intususcepted balloon for including debris particles and plaque particulates within the space formed, one needs to increase the length of the balloon. However, the length of an inflatable balloon having a uniform cross-sectional area will disadvantageously also increase the length of the balloon surface in contact with the blood vessel walls during the fully inflated state of the balloon. Moreover, from the clinical point of view, it is desirable to minimize the length of the balloon portion which would be placed in direct contact with the surface of the blood vessel during the plaque treatment phase (in which the balloon is expanded), as one would like to minimize the possible damage to the blood vessel wall which may be caused by the expansion of the balloon and its contact with the plaque and the associated blood vessel wall.

Thus, there is a need to increase the total volume within the internal space of the balloon in its intussuscepted (invaginated) state, without overly increasing the area of contact of the fully inflated balloon with the walls of the blood vessel during plaque treatment.

SUMMARY OF THE INVENTION

There is therefore provided, in accordance with an embodiment of the balloon catheters of the present application a balloon catheter. The balloon catheter includes an outer conduit, an inner conduit suitable for passage over a guide wire. The inner conduit is disposed within the lumen of the outer conduit such that the longitudinal axes of the inner and outer conduits are substantially parallel, and is positioned such that the distal tip of the inner conduit extends beyond the distal tip of the outer conduit. The inner conduit is capable of being moved along its longitudinal axis in relation to the outer conduit. The balloon catheter also includes an inflatable balloon having a proximal margin attached to the outer surface of the distal tip of the outer conduit, and a distal margin attached to the outer surface of the portion of the inner conduit that extends beyond the distal tip of the outer conduit. The inflatable balloon includes a cylindrical middle portion, an inflatable distal side portion having at least one tapering part, and an inflatable proximal side portion having at least one tapering part. The length of the inflatable proximal side portion is equal to or larger than the length of the middle portion. The distal end portion of the balloon is capable of intussuscepting upon proximal movement of the inner conduit in relation to the outer conduit. The balloon catheter also includes a fluid port for introducing an inflation fluid into the space formed between the inner surface of the outer conduit and the outer surface of the inner conduit and into the lumen of the balloon, and for removing the inflation fluid from the space and from the lumen.

Furthermore, in accordance with an embodiment of the balloon catheter of the present application, the proximal side portion includes at least a second cylindrical portion having in the inflated state a diameter smaller than the diameter of the middle portion in the inflated state.

Furthermore, in accordance with an embodiment of the balloon catheter of the present application, wherein said proximal portion also comprises at least two frusto-conical portions flanking the distal and the proximal sides of said second cylindrical portion.

Furthermore, in accordance with an embodiment of the balloon catheter of the present application, said proximal portion comprises at least one frusto-conical portion.

Furthermore, in accordance with an embodiment of the balloon catheter of the present application, the inflatable proximal portion includes one or more portions selected from, cylindrical portions, frusto-conical portions, concave tapering portions, convex tapering portions, and combinations thereof.

Furthermore, in accordance with an embodiment of the balloon catheter of the present application, the length of the inflatable proximal side portion is equal to or larger than the combined length of the middle portion and the inflatable distal portion.

Furthermore, in accordance with an embodiment of the balloon catheter of the present application, at least part of the inflatable balloon is a corrugated part.

Furthermore, in accordance with an embodiment of the balloon catheter of the present application, the corrugated part is selected from, at least a portion of the inflatable distal portion of said balloon, at least a part of the middle portion of the balloon, and at least a part of the inflatable distal portion and the middle portion of the balloon.

Furthermore, in accordance with an embodiment of the balloon catheter of the present application, said balloon has a non-uniform wall thickness along its longitudinal axis.

Furthermore, in accordance with an embodiment of the balloon catheter of the present application, the wall thickness of at least part of the inflatable distal portion is smaller than the wall thickness of at least part of the middle portion of the balloon.

Furthermore, in accordance with an embodiment of the balloon catheter of the present application, the wall thickness of at least part of the inflatable distal portion is smaller than the wall thickness of at least part of the inflatable proximal portion of the balloon.

Furthermore, in accordance with an embodiment of the balloon catheter of the present application, the wall thickness of at least part of the inflatable distal portion is smaller than the wall thickness of at least part of the middle portion of the balloon.

Furthermore, in accordance with an embodiment of the balloon catheter of the present application, the inflatable distal portion of the inflatable balloon includes one or more portions selected from dome-like portions, truncated dome-like portions, conical portions, frusto-conical portions, corrugated dome-like portions, corrugated conical portions, corrugated frusto-conical portions, corrugated truncated dome-like portions and combinations thereof.

Furthermore, in accordance with an embodiment of the balloon catheter of the present application, the balloon catheter also includes a pressure adjusting mechanism for preventing substantial pressure changes within the space and the lumen of the balloon upon axial movement of the inner conduit in relation to the outer conduit.

Furthermore, in accordance with an embodiment of the balloon catheter of the present application, the pressure adjusting mechanism is selected from, a pressure adjusting mechanism including a syringe-like structure disposed at the proximal end of the balloon catheter. The syringe-like structure includes a barrel and a plunger disposed within the barrel. The plunger co-axially surrounds the proximal end of the inner conduit, and is affixed thereto, an outlet in fluidic communication with the lumen of the inflatable balloon and having an opening and a compliant member sealingly attached to the opening for at least partially relieving over-pressure in the lumen, an over-pressure valve outlet in fluidic communication with the lumen of the inflatable balloon and an over-pressure valve disposed within the over-pressure outlet to allow discharging of fluid from the lumen when over-pressure conditions develop in the lumen, and an expandable or inflatable portion of the outer conduit, capable of being inflated when over-pressure conditions occur in the lumen of the balloon to at least partially relieve the over-pressure in the lumen.

There is also provided in accordance with the methods of the present application a method of constructing an intussusceptible balloon catheter. The method includes the steps of:

providing a catheter having an outer conduit and an inner conduit, suitable for passage over a guide wire. The inner conduit is disposed within the lumen of the outer conduit such that the longitudinal axes of the inner and outer conduits are substantially parallel. The inner conduit is positioned such that the distal tip thereof extends beyond the distal tip of the outer conduit. The inner conduit is capable of being moved along its longitudinal axis in relation to the outer conduit. The catheter has an inflation fluid port in fluidic communication with the space formed between the inner surface of the outer conduit and the outer surface of the inner conduit, providing an inflatable balloon having a proximal margin and a distal margin, the balloon includes a cylindrical middle portion having a first diameter in the fully inflated state. The balloon also includes an inflatable distal side portion having at least one tapering part and an inflatable proximal side portion having at least one tapering portion. The length of the inflatable proximal side portion is equal to or larger than the length of the middle portion. The distal end portion of the balloon is capable of intussuscepting upon proximal movement of the inner conduit in relation to the outer conduit, and sealingly attaching the proximal margin of the balloon to the outer surface of the distal end of the outer conduit and sealingly attaching the distal margin of the balloon to the outer surface of the portion of the inner conduit that extends beyond the distal end of the outer conduit such that the lumen of the balloon is in fluidic communication with the space. The attaching is performed such that the distal end portion of the balloon is capable of intussuscepting upon proximal movement of the inner conduit in relation to the outer conduit.

There is also provided in accordance with the methods of the present application, a method for collecting debris from an internal passage of a mammalian subject. The method includes the steps of:

inserting a balloon catheter including a balloon as described above into the internal passage and advancing the catheter until the distal tip thereof has reached the site, at which it is desired to collect debris, inflating the balloon with expansion fluid, pulling the inner conduit of the balloon catheter in a proximal direction, for collapsing the distal end of the balloon to form a cavity within the balloon into which debris is collected and entrapped, deflating the intussuscepted balloon, and removing the deflated balloon catheter from the internal passage of the subject, together with the entrapped debris.

Furthermore, in accordance with an embodiment of the method, the internal passage is a blood vessel.

Furthermore, in accordance with an embodiment of the method, the step of pulling includes pulling the inner conduit of the balloon catheter in a proximal direction to form the cavity, such that all of the surface portions of the middle portion are internally disposed within the cavity to enhance retention of the debris.

Furthermore, in accordance with an embodiment of the method, the catheter includes a mechanism for preventing substantial pressure changes when the inner conduit is moved proximally within the outer conduit while the balloon is inflated and the fluid port is closed, and the step of pulling includes pulling the inner conduit of the balloon catheter in a proximal direction for collapsing the distal end of the balloon to form a cavity within the balloon into which the debris is collected and entrapped, without causing substantial pressure changes within the lumen of the balloon during the step of pulling.

There is also provided in accordance with an embodiment of the sleeve-like element of the present application, a stepped tapered element for use in constructing a catheter. the element includes a sleeve-like element including a cylindrical middle portion, an inflatable distal side portion having at least one tapering part and an inflatable proximal side portion having at least one tapering part. The length of the inflatable proximal side portion is equal to or larger than the length of the middle portion. The proximal side portion has a first open end with a first diameter and the distal side portion has a second open end with a second diameter smaller than the first diameter. The length of the inflatable proximal side portion is equal to or larger than the length of the middle portion.

Furthermore in accordance with an embodiment of the sleeve-like catheter element of the present application, the inflatable proximal portion includes at least a second cylindrical portion having in the inflated state a diameter smaller than the diameter of the middle portion in the inflated state.

Furthermore in accordance with an embodiment of the sleeve-like catheter element of the present application, the inflatable proximal portion also includes at least two frusto-conical portions flanking the distal and the proximal sides of the second cylindrical portion.

Furthermore in accordance with an embodiment of the sleeve-like catheter element of the present application, the inflatable proximal portion includes at least one frusto-conical portion.

Furthermore in accordance with an embodiment of the sleeve-like catheter element of the present application, the inflatable proximal portion includes one or more portions selected from, cylindrical portions, frusto-conical portions, concave tapering portions, convex tapering portions, and combinations thereof.

Furthermore in accordance with an embodiment of the sleeve-like catheter element of the present application, the length of the inflatable proximal side portion is equal to or larger than the combined length of the middle portion and the inflatable distal portion.

Furthermore in accordance with an embodiment of the sleeve-like catheter element of the present application, at least part of the sleeve-like element is a corrugated part.

Furthermore in accordance with an embodiment of the sleeve-like catheter element of the present application, the corrugated part is selected from, at least part of the inflatable distal portion of the element, at least part of the middle portion of the element, and at least part of the inflatable distal portion and the middle portion of the element.

Furthermore in accordance with an embodiment of the sleeve-like catheter element of the present application, the element has a non-uniform wall thickness along its longitudinal axis.

Furthermore in accordance with an embodiment of the sleeve-like catheter element of the present application, the wall thickness of at least part of the inflatable distal portion is smaller than the wall thickness of at least part of the middle portion of the element.

Furthermore in accordance with an embodiment of the sleeve-like catheter element of the present application, the wall thickness of at least part of the inflatable distal portion is smaller than the wall thickness of at least part of the inflatable proximal portion of the element.

Furthermore in accordance with an embodiment of the sleeve-like catheter element of the present application, the wall thickness of at least part of the inflatable distal portion is smaller than the wall thickness of at least part of the middle portion of the element.

Furthermore in accordance with an embodiment of the sleeve-like catheter element of the present application, the inflatable distal portion of the element includes one or more portions selected from dome-like portions, truncated dome-like portions, conical portions, frusto-conical portions, corrugated dome-like portions, corrugated conical portions, corrugated frusto-conical portions, corrugated truncated dome-like portions and combinations thereof.

Furthermore in accordance with an embodiment of the sleeve-like catheter element of the present application, the shape of the inflatable distal side portion of the sleeve-like element is selected from a dome-like shape, a truncated dome-like shape, a conical shape, a frusto-conical shape, a corrugated dome-like shape, a corrugated conical shape a corrugated frusto-conical shape, and a corrugated truncated dome-like shape.

BRIEF DESCRIPTION OF THE DRAWINGS

The invention is herein described, by way of example only, with reference to the accompanying drawings, in which like components are designated by like reference numerals, wherein:

FIGS. 2-6 are schematic cross-sectional diagrams illustrating a catheter system including an intussusceptible balloon having a stepped tapering structure and several different steps of a method for using the catheter system for treating atheromatous plaque in a blood vessel and for removing fluid and/or debris particles out of the treated blood vessel, in accordance with an embodiment of the catheter system and method of use thereof of the present application;

DETAILED DESCRIPTION OF THE INVENTION

Notation Used Throughout

Figure 1:
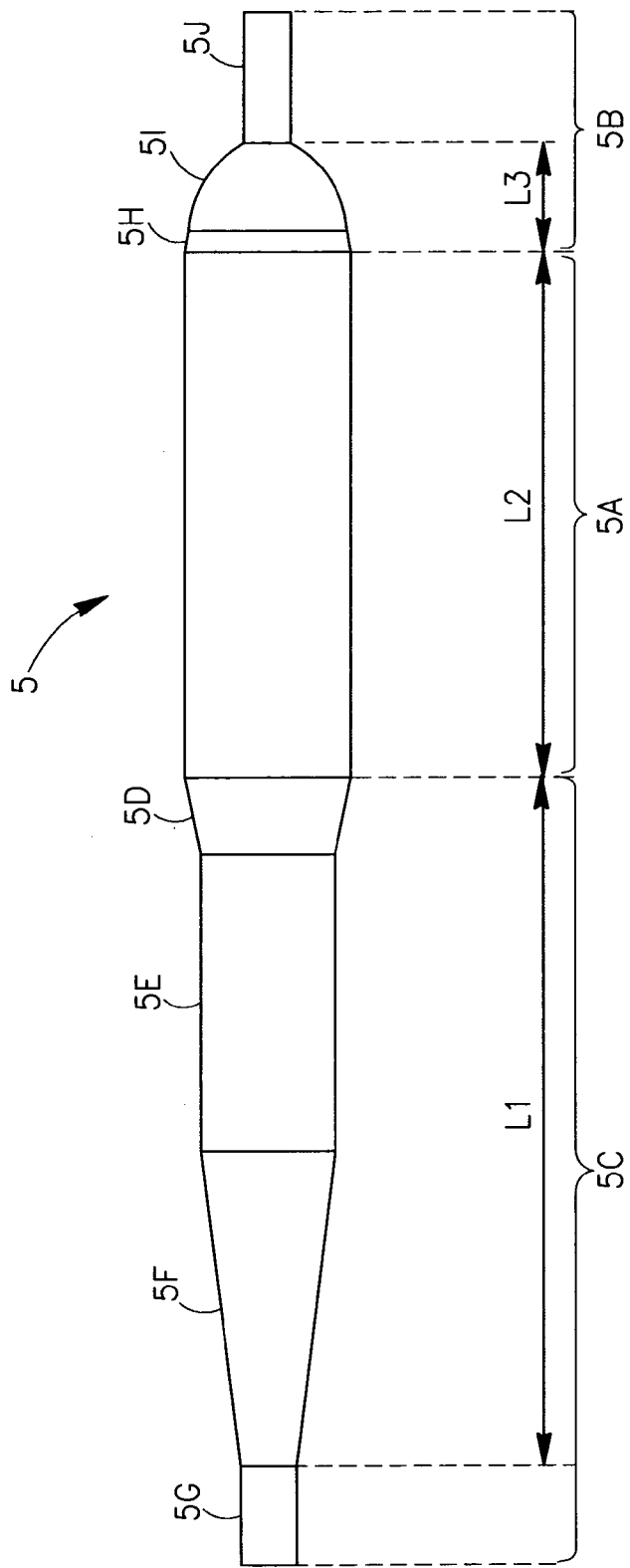
FIG. 1 is a schematic side view of a tapered stepped sleeve-like element usable in a balloon catheter having an expandable intussusceptible tapering stepped balloon, in accordance with one embodiment of the balloon catheters of the present application.

The following notation is used throughout this document.

| Term | Definition |
| --- | --- |
| DCA | Directional coronary atherectomy |
| ELCA | Excimer Laser Coronary Angioplasty |
| mm | millimeter |
| PA | Polyamide |
| PE | Polyethylene |
| PET | Polyethylene terephtalate |
| PLOSA | Physiologic low stress angioplasty |

It is noted that in the following description and in the claims of the present application, the terms "distal" and "proximal" are defined as follows: the catheter side or end which is inserted into the body first is referred to as the distal side or distal end and the trailing side or end of the catheters part of which remains outside the body after insertion of the catheter is referred to as the proximal side. For example, in the balloon catheter 10 of FIG. 2, the graduated scale 19 is disposed on the proximal side of the catheter 10 and the cylindrical portion 5J is disposed near the distal side or distal end of the catheter 10.

Similarly, when referring to sides, parts or portions of the stepped balloons (or stepped sleeve-like elements) of the catheters of the present application, the term distal refers to a part, end or portion of the stepped balloon (or stepped sleeve-like element) which is inserted first into the body when the balloon catheter is operated. For example, the balloon 10 of FIGS. 1-2 has a middle portion 10A, a proximal side portion 10B and a distal side portion 10C.

It is further noted that the terms "inner tube" and "inner conduit" are interchangeably used throughout the specification and the claims of the present application and refer to the same component. Similarly, the terms "outer tube" and "outer conduit" are interchangeably used throughout the specification and the claims of the present application and refer to the same component.

It is also noted that the terms "sleeve-like element" and "balloon" in the singular and plural forms are interchangeably used in the present application. The term "sleeve-like element" is typically used throughout the application to refer to the element or balloon before it is assembled into the balloon catheter, while the term "balloon" is used to refer to the same sleeve-like element after it has been assembled into the balloon catheter.

The present application discloses catheters and systems including balloon-like controllably inflatable and controllably intussusceptible members having non-uniform cross-sectional areas along their longitudinal dimension. Such balloons may include a middle cylindrical balloon portion having a first diameter designed for contacting the walls of a body passage (such as, but not limited to, a blood vessel), and one or more non-contacting side portions extending longitudinally on one or more sides of the middle portion. The one or more non-contacting portions are designed and implemented such that when the entire balloon is fully inflated, the maximal transversal dimensions of the side portion(s) is (are) smaller than the transversal dimension (diameter) of the middle portion of the balloon. The side portion(s) may have cylindrical and/or conical and/or frusto-conical, and/or rounded dome-like and/or tapering shape(s). The side portion(s) may also have a shape which is a combination of one or more of cylindrical, conical, frusto-conical, dome-like and tapering shapes.

Reference is now made to FIG. 1 which is a schematic side view of an expandable balloon having a stepped structure in accordance with one embodiment of the balloons of the present application. It is noted that while the balloon 5 of FIG. 1 is shown without a catheter or catheter system attached to it for better understanding of its structure, the balloon 5 may be suitably attached to a catheter or catheter system as disclosed in detail hereinafter (See, for example, FIGS. 2-5 of the present application).

The stepped balloon 5 of FIG. 1 is preferably a flexible resilient sleeve that includes a plaque treating portion 5A and two (non-plaque treating) side portions 5B and 5C. In the specific (and non-limiting) embodiment of balloon 5 illustrated in FIGS. 1-6, the plaque treating portion 5A is shaped as a cylinder, and the balloon side portion 5C includes a frusto-conical portion 5D, a cylindrical portion 5E, a frusto-conical portion 5F and a cylindrical portion 5G. The cylindrical portion 5G is the proximal margin of the balloon 5.

It is noted that the side portion 5C is configured such that the diameters of the cylindrical portion 5E and the frusto-conical portion 5F are substantially smaller than the diameter of the plaque treating portion 5A. The side portion 5B of the balloon 5 includes a frustoconical portion 5H, a truncated dome-like portion 5I and a cylindrical portion 5J. The cylindrical portion 5J is the distal margin of the balloon 5.

Preferably the balloon 5 is made from Nylon or another suitable biocompatible material, as is known in the art, such as, but not limited to, PET, PA12 (for example Grilamid® L25, L55 and the like), PA11, PABA, Polyether block amides (such as for example, PEBAX® 7233, 7033, 6333), various types of Grilflex® (such as, for example, ELG 6260), and the like. However, any other suitable material known in the art and suitable for fabrication of catheter balloons may be used in implementing the balloons of the present application.

Reference is now made to FIGS. 2-6 which are schematic cross-sectional diagrams illustrating a catheter system with an improved balloon and several different steps of a method for using the catheter system for treating atheromatous plaque in a blood vessel and for removing fluid and/or debris particles out of the treated blood vessel, in accordance with an embodiment of the catheter system and method of use thereof of the present application.

In the following description, the terms "conduit" and "tube" are used interchangeably.

FIG. 2 illustrates the insertion of the balloon catheter 10 of the present application to a treatment site, for example a blood vessel 20. It is noted that while the illustrations of the application use the blood vessel 20 as an example of the treated site, this is done by way of exemplary demonstration only, and other body passages may also be treated by the catheters, and catheter systems of the present application. The balloon catheter 10 comprises an inner tube 17 slidably positioned inside an outer tube 18. The proximal (i.e., trailing) end of inner tube 17 comprises an entry port 12, which extends outwardly through orifice 29 provided at the proximal end of the outer tube 18. Orifice 29 tightly fits around the outer surface of inner tube 17 without gripping it, thereby allowing proximal and distal movements of inner tube 17 while sealing the inner lumen of outer tube 18.

It is noted that a graduated scale 19 may optionally be provided on the outer surface of inner tube 17 as illustrated and described in detail in the above referenced PCT application published as WO 2007/7004221 and as explained hereinafter with reference to FIG. 4 of the present application.

The proximal end of outer tube 18 further comprises a fluid port 11 for injecting/removing inflation fluids to/from inner lumen of outer tube 18, an over-pressure valve outlet 15 for discharging inflation fluids whenever over-pressure conditions develop in the inner lumen of outer tube 18, and an inner tube safety lock 14 adapted for gripping the outer surface of inner tube 17, thereby preventing proximal-distal movements thereof relative to outer tube 18.

The over-pressure valve outlet 15 may include an over-pressure valve 16 for sealing the opening of over-pressure valve outlet 15 and for discharging portions of inflating fluids therethrough whenever over-pressure conditions are reached in inner lumen of outer tube 18. The over-pressure valve outlet 15 is in fluidic communication with the lumen of the inflatable balloon 5 through the space formed between the inner surface of the outer tube 18 and the outer surface of the inner tube 17. The over-pressure valve 16 disposed within the over-pressure outlet 15 may allow discharging of fluid from the lumen of the balloon 10 when over-pressure conditions develop in the lumen of the balloon 10 during the intussuscepting of the balloon 10.

It should be realized however that such over-pressure conditions may be resolved by other means. For example, a compliant member (not shown) may be attached to the opening of over-pressure valve outlet 15, and in such an implementation over-pressure valve 16 may be eliminated (see FIG. 15 below for a detailed description). Moreover, outer tube 18, or portions thereof, may be inflatable such that over-pressure conditions may be resolved by its expansion.

The inner tube safety lock 14 contacts the outer surface of inner tube 17 via a tight orifice provided on the outer surface at the proximal end of outer tube 18. It is noted that the details of construction and operation of the safety lock 14 are fully explained and illustrated in FIGS. 1A and 1B of the above referenced PCT application published as WO 2007/7004221, and are therefore not disclosed in detail hereinafter.

As seen in FIG. 2, the distal (leading) end of inner tube 17 extends outwardly through the distal opening of outer tube 18, into the blood vessel 20. An inflatable member, for example a semi-compliant or non-compliant balloon 5 (of FIG. 1), is attached to the distal ends of outer tube 18 and the inner tube 17. The portion 5G of the balloon 5 is attached at circumferential attachment region 7 to the outer surface near the distal tip of outer tube 18. The portion 5J of the balloon 5 is attached at circumferential attachment region 6 to the outer surface near the distal tip of inner tube 17, such that it seals the distal opening of the outer tube 18. The attachment of the balloon 5 to the tips of the inner tube 17 and the outer tube 18 may be implemented using any suitable sealing attachment method known in the art, including but not limited to heat bonding, welding, ultrasonic welding, gluing, or any other method known in the art and capable of producing a sealed attachment capable of withstanding the pressures required for operating the inflatable expandable balloon(s) of the present application.

In accordance with another embodiment of the catheters of the present application, the catheter may include a pressure adjusting mechanism comprising a syringe-like structure. The syringe-like structure is disposed at the proximal end of the balloon catheter. The syringe-like structure may include a barrel and a plunger disposed within the barrel. The plunger co-axially surrounds the proximal end of the inner conduit 17, and is affixed thereto. This embodiment is fully disclosed in detail in the above referenced International Patent application published as WO 2007/7004221 incorporated herein by reference in its entirety (in FIG. 1C thereof), and is therefore not described in detail hereinafter. Briefly, the syringe-like structure of FIG. 1C of WO 2007/7004221 is positioned at the proximal end of the catheter system, wherein the barrel portion 26 (of FIG. 1C of WO 2007/7004221) of the syringe-like structure is formed by an expanded portion of the outer conduit 18, and wherein the plunger 17a (of FIG. 1C of WO 2007/7004221) of the syringe-like structure co-axially surrounds the proximal end of the inner conduit 17. However, the barrel portion 26 may also be implemented as a separate member suitably sealingly attached to the outer conduit 18.

Turning back to FIG. 2, an exemplary interventional procedure using the stepped balloon catheter 10 of the present application starts as the balloon catheter 10 is guided to the treatment site within the blood vessel 20 (e.g., over the wire). FIG. 2 illustrates over-the-wire insertion, wherein the insertion of the balloon catheter 10 is performed over a guide wire 13. It should be clear, however, that the invention is not limited to one specific insertion method and that other appropriate and practicable catheter insertion methods known in the art (such as, but not limited to, using a guiding catheter) may also be used. The catheter is advanced over the guide wire 13 until the (non-inflated) middle portion 5A is positioned within the atheromatous plaque 23 attached to the inner surface 21 of the blood vessel 20.

Turning to FIG. 3, the operator inflates the balloon 5 by injecting inflation fluids via fluid port 11 and the inner lumen of outer tube 18, as demonstrated by fluid inflation arrows 8A in FIG. 2. When carrying out procedures in blood vessel 20 as demonstrated in the FIGS. 2-6, inflation fluids are preferably injected into the balloon 5 such that the circumferential sides of portion 5A of the balloon 5 are expanded and pressed against the inner surface 21 of blood vessel 20 and against the plaque 23, as illustrated in FIG. 3. The pressure inside balloon 5 in such conditions may be in general about 1-25 Atmospheres, preferably about 6 Atmospheres.

It is noted that while in the embodiment of the treatment method illustrated in FIGS. 2-6 the portion 5A of the balloon is placed within the plaque 23 and is used to treat the plaque 23 by pushing the plaque towards the walls of the blood vessel 20 to open a larger passage within the atheromatous portion of the blood vessel 20, other different treatment methods are also possible, in which the portion 5A is not used as a plaque treating or plaque pushing means, but is used as an anchoring portion of the balloon 5 enabling firm anchoring of the catheter 10 which in turn allows other different plaque treating devices (not shown in FIG. 2-6) to be inserted into the lumen of the inner tube 17 (after withdrawal of the guide wire 13) for treating the plaque. In such alternative treatment methods, the portion 5A of the balloon is typically positioned within the blood vessel 20 at a site proximal to the position of the plaque 23, and plaque treatment is performed by an additional treating device (such as, but not limited to, a rotablator burr, a mechanical cutting device, a laser device such as an excimer laser or other laser for performing ELCA or other types of laser based atherectomies, Radiofrequency angioplasty device, an ultrasonic ablator device, and the like) inserted into the lumen of the inner tube 17.

In this state in which the balloon catheter 10 is anchored, the inner lumen of inner tube 17 may now be utilized for operating in the treated site with different interventional tools (not shown in FIGS. 2-6)), as may be required. However, some procedures (for example angioplasty) may be completed, or may be near completion, once balloon 5 reaches its inflated state.

Irrespective of which particular method of plaque treatment is used, after plaque treatment is achieved, a sample of liquid or solid matter, for example fluids, secretions, and/or debris 25 (resulting from plaque breakup due to treatment steps) may be collected and removed from the treatment site by causing the balloon 5 to intussuscept. The inner tube safety lock 14 is pulled in the direction illustrated by arrow 27A in FIG. 3, thereby releasing its grip from inner tube 17. The inner tube 17 is then retracted outwardly (proximally) by the operator as shown by arrow 28. During retraction of inner tube 17 the distal portion of balloon 5 collapses and the outer surface portions of the balloon 5 are folded inwardly over the distal tip of inner tube 17 and thereafter over itself as further portions of the balloon collapse, as illustrated in FIGS. 4-5.

The retraction of the inner tube 17 and the resulting inward folding of balloon 5 shortens the overall length of inflated balloon 5 which actually reduces the volume of inflated balloon 5. Consequently, the pressure exerted by the inflating fluids increases, resulting in a considerable pressure increase in the balloon 5 and inner lumen of outer tube 18. Whenever the pressure in the balloon 5 and the inner lumen of outer tube 18 reaches a certain set-point (e.g., 5-20 atmospheres) inflation fluids flow towards the proximal side of the balloon 5 (as indicated by arrows 8C of FIG. 4), and are discharged via over-pressure valve outlet 15, as shown by arrows 8B of FIG. 4, such that the pressure in the balloon 5 and the inner lumen of outer tube 18 remains within a predetermined pressure range (e.g., 5-20 atmospheres). Optionally, in catheters including the graduated scale 19, the operator can determine by monitoring the graduated scale 19, the amount of length of the inner tube 17 that has been retracted and in this way the operator may determine when to stop the retraction and restore immobilization (locking) of the inner tube 17 by pushing down the inner tube safety lock 14, in the direction indicated by the arrow 27B.

Figure 6:
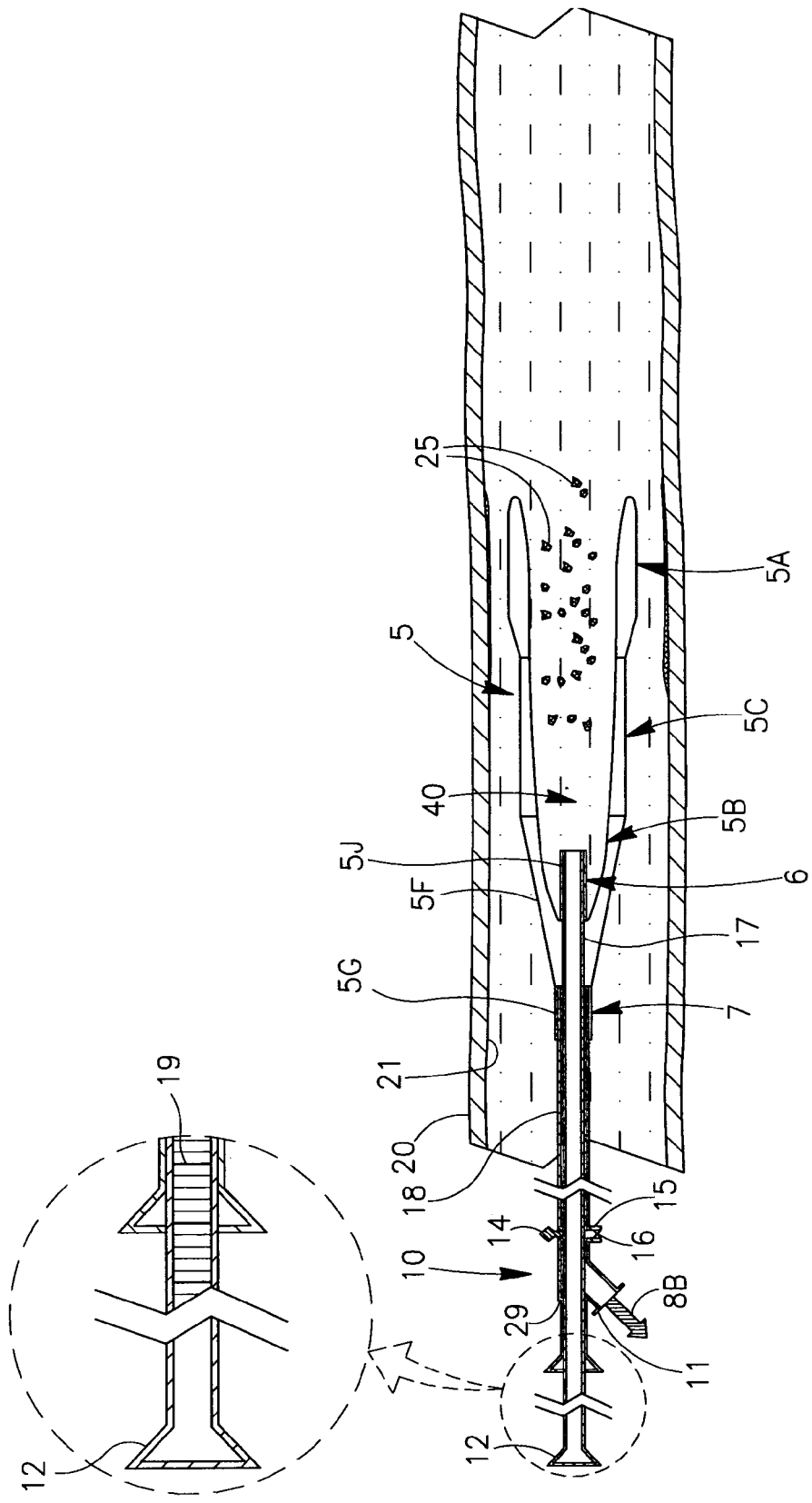

After the intussuscepting of the balloon 5 has been completed, the balloon 5 is deflated by retracting inflation fluids through the fluid port 11, as indicated by arrows 8C in FIG. 6. In result, the pressure inside balloon 5 and in the inner lumen of outer tube 18 is substantially decreased, and the intussuscepted balloon 5 is deflated. The reduction in the volume of the balloon 5 results in the formation of an inner lumen 40 defined by the formerly outer surface of the folded balloon part, as shown in FIGS. 4-6. After the intussuscepting and deflation of the balloon 5, the operator may retract (withdraw) the balloon catheter 10 proximally such that the portion of fluid/secretion and debris 25 confined within the inner lumen 40 are withdrawn with the balloon catheter 10 outside of the treated body (not shown in the figures). The debris, objects or samples collected may be easily collected when the entire length of balloon catheter 10 is withdrawn from the body of the treated subject, by pushing the inner tube 17 distally and unfolding the folded portions of balloon 5, thus restoring the deflated state of balloon 5 (shown in FIG. 2).

In certain embodiments of the catheters of the present application (not shown in Fig., there is no the over-pressure adjusting mechanism and the over-pressure may be resolved by slight expansion of some parts of the catheter (such as but not limited to, the outer conduit 18) if these parts are made of sufficiently compliant material. While in some embodiments of the catheters of the present application, the pressure inside the lumen of the balloon 10 may increase during the intussuscepting of the balloon, such pressure increase may be safely accommodated by using a balloon 5 capable of safely withstanding the over-pressure resulting from the intussuscepting of the balloon 5. For example, the wall thickness of the balloon 5 may be made sufficiently thick to safely withstand the over-pressure or the balloon 5 may be made from a material having sufficient strength to effectively withstand the over-pressure resulting from the intussuscepting of the balloon 5.

In view of the axially-directed stretching and buckling forces exerted on the inner and outer tubes during elongation and shortening of the balloon, said tubes need to be constructed such that they are able to withstand axially-directed forces in the range of between 2 and 20 Newton without undergoing deformation. In order to achieve this aim, the conduits may be constructed of a braided material or of materials having a defined molecular orientation. The approximate maximum forces that the inner and outer tubes need to withstand (for two difference size ranges of balloon inflated diameter. The inflated diameter is defined as the diameter of the balloon midsection at the balloon's nominal pressure) are as follows:

I) 2.5-4 mm diameter balloons: the tubing should withstand forces of up to 500 g; polymer tubing made of Nylon or Pebax® (a thermoplastic polyether block amide polymer) reinforced during the manufacturing process can be used.

II) 4-8 mm diameter (or larger) balloons: the tubing should withstand forces up to 2 kg. In this case it may be necessary to use a braided tube (polymer tube with metal mesh reinforcement).

Exemplary results for a representative study of the forces generated during balloon folding are presented in Example 2, of WO 2007/7004221 incorporated herein by reference in its entirety.

The outer tube 18 is preferably made from a biocompatible polymer type of material, such as polyurethane or nylon or PET, and may be manufactured using conventional methods, such as extrusion. The diameter of the inner lumen of outer tube 18 is generally in the range of 0.5-2.0 mm (millimeters), preferably about 0.7 mm, and the diameter of the fluid port 11 is generally in the range of 2-6 mm, preferably about 4 mm. The diameter of the over-pressure valve outlet 15 is generally in the range of 1-6 mm, preferably about 4 mm, and the entire length of the outer tube 18 is generally in the range of 100-2000 mm, preferably about 1400 mm.

The inner tube 17 is preferably made from a biocompatible polymer type of material, such as polyurethane or Nylon or PET, and it may be manufactured using conventional methods, such as extrusion. The diameter of the inner lumen of inner tube 17 is generally in the range of 0.2-2.0 mm, preferably about 0.5 mm, and its entire length is generally in the range of 100-2000 mm, preferably about 1500 mm.

However, it will be appreciated by those skilled in the art that all values and dimensions of the various parts of the catheters and the values of the forces acting on the various parts as disclosed herein, are given by way of practical examples only and it may be possible to implement the catheters and balloons of the present invention by using other different values and/or value ranges of dimensions of the various parts of the catheters and/or forces to be withstood by such parts and/or different structural materials for constructing and implementing the catheters disclosed herein and any of their parts and/or components.

While the diameter of the orifice 29 provided at the proximal tip of the outer tube 18 should be adapted to provide appropriate sealing of inner lumen of the outer tube 18 it should also close over the outer surface of the inner tube 17 such that inner tube 17 may be displaced therethrough with relatively low frictional forces. For example, if the diameter of the inner tube 17 is 0.7 mm, then the diameter of the orifice 29 should be 1.0 mm.

The Balloon 5 is preferably a semi-compliant or non-compliant balloon such as the balloons manufactured by Advanced Polymers (Salem, USA) and by Interface Associates (CA). It may be manufactured using conventional methods known in the balloon catheter industry from a non-compliant type or a semi-compliant of material such as Pebax® or Nylon (preferably Nylon 12), but any other suitable material may also be used. The length of the balloon 5 is generally in the range of 10-60 mm, preferably about 20 mm. The diameter of the cylindrical portion 5A of the balloon 5 can vary from 2.0 mm to 5 mm for coronary artery applications, but may be significantly larger for use in larger blood vessels. Preferably, the balloon 5 should have a burst pressure within the range of 12-20 atmospheres. The proximal and distal edges of balloon such as the cylindrical portions 5G and 5J, respectively, of the balloon 5, are preferably sealingly attached to the outer surfaces of outer tube 18 and of the inner tube 17 respectively, at circumferential attachment points 7 and 6 respectively, by using a UV or thermobonding type of adhesive such as commonly used in the art.

The shape of balloon 5 has been found by the present inventors to be important in order for the balloon to fulfill its intended functions in the presently-disclosed and claimed catheter system, namely:

1) to facilitate folding in such a way that the desired annular space is formed at the distal end of the intussuscepted balloon, by the application of the lowest possible retracting force;

2) to present a low profile that will facilitate introduction and withdrawal of the deflated balloon into and out of the catheter system and body passage or blood vessel.

3) to increase the volume 40 of the lumen formed within the folded (intussuscepted) balloon, while keeping the total surface of the balloon (in it's fully inflated state) that will be placed in contact with the blood vessels walls (and/or with the plaque) as small as possible for fulfilling its treating and/or anchoring intended function(s) and while enabling the maintaining of a seal between the blood vessel wall and at least part of the inflated portion of the balloon 5 having the largest diameter.

The materials and design of the balloon, especially the shape of the distal taper and the relationship between the distal and the proximal taper, thus allow the balloon to fold smoothly and with relatively low pulling forces. This also insures that the balloon will fold only its distal side.

It appears, from modeling studies performed by the inventors, that a tapered balloon with smooth round ending folds best and has a relatively low retracting force, when compared to standard tapered balloon or a balloon with a round ending. In a particularly preferred embodiment, the balloon has a proximal taper cone shaped with a 15-17 degree angle, and a 15 degree round cone distal taper, having a radius of about 0.5 mm at the junction of the taper and the neck. The results of the aforementioned modeling studies are presented in Example 2 of PCT international application published as publication number WO 2007/7004221.

Turning back to FIG. 1, the inflatable proximal portion of the balloon 5 includes the frusto-conical portion 5D, the cylindrical portion 5E, and the frusto-conical portion 5F (the cylindrical portion 5G is sealingly attached to the outer tube 18 and is therefore not included in the inflatable proximal portion of the balloon 5), and has a length of L1. The cylindrical inflatable middle portion 5A has a length L2. The inflatable distal portion of the balloon 5 includes the frusto-conical portion 5H, and the truncated dome-like portion 5I, and has a length L3 (the cylindrical portion 5J of the side portion 5B is sealingly attached to the inner tube 17 and is therefore not included in the inflatable distal portion of the balloon 5).

It is noted that similarly, for all the balloons illustrated in the drawing figures of the application, the cylindrical portions 50J, 60H, 70H, 80H, 90H, 170H and 180H are not included in the inflatable proximal portions of the balloons 50, 60, 70, 80, 90, 170 and 180, respectively as they are glued or welded or otherwise sealingly attached to the outer tube 18.

Similarly, for all the balloons illustrated in the drawing figures of the application, the cylindrical portions 50D, 60D, 70D, 80D, 90J, 170J and 180J are not included in the inflatable distal portions of the balloons 50, 60, 70, 80, 90, 170 and 180, respectively, as they are glued or welded or otherwise sealingly attached to the inner tube 17.

It is therefore noted that the terms "distal portion" and "inflatable distal portion" are not identical and define different portions of the balloon in the specification and the claims of the present application. Similarly the terms "proximal portion" and "inflatable proximal portion" are not identical and define different portions of the balloon in the specification and the claims of the present application.

It is further noted that the cylindrical portions 50J, 60H, 70H, 80H, 90H, 170H and 180H are also referred to as the proximal margins of the of the balloons 50, 60, 70, 80, 90, 170 and 180, respectively, throughout the specification and the claims of the present application.

Similarly, it is also noted that the cylindrical portions 50D, 60D, 70D, 80D, 90J, 170J and 180J are also referred to as the distal margins of the of the balloons 50, 60, 70, 80, 90, 170 and 180, respectively, throughout the specification and the claims of the present application.

With respect to achieving the desired function goals detailed in item iii above, the inventors of the present application has found that it is preferable to maintain certain relationships between the various portions of the balloon 5 as follows: Preferably, the length L1 should be larger than the length L2 by at least 2-3 millimeters. Even more preferably, the length L1 should, be larger than the combined lengths L2+L3 by at least 2-3 millimeters. It is however noted, that while these relationships are found to be advantageous, the improved balloons disclosed herein may also be practiced with some changes from these length relationships, sacrificing full optimization of the volume 40 in order to ensure the maintaining of a good sealing between the balloon and the walls of the blood vessel 20 or to achieve other different balloon design parameters.

The inner tube safety lock 14 is preferably made from a biocompatible polymer such as Tecoflex®, or other suitable biocompatible polymers materials. The length of the inner tube safety lock 14 is generally in the range of 1-15 mm, preferably about 5 mm. If, for example, the cross-sectional diameter of the inner tube safety lock 14 is about 2 mm, then the orifice provided on the outer surface of outer tube 18 through which inner tube safety lock 14 accesses the inner lumen of the outer tube 18 is preferably about 2.4 mm for providing suitable sealing of the inner lumen of the outer tube 18.

It is noted that the shape and number and configuration of portions of the Balloon 5 of FIGS. 1-6 are given by way of example only and that other types of balloons, having different configurations, arrangements and numbers of balloon portions, may be implemented and used in the catheters of the present application. A number of non-limiting, examples of such improved balloons are illustrated in FIGS. 7-10 hereinbelow. Reference is now made to FIGS. 7-10 which are schematic side views, illustrating various different possible embodiments of inflatable balloons suitable for use in the catheters and catheter systems of the present application.

Figure 7:
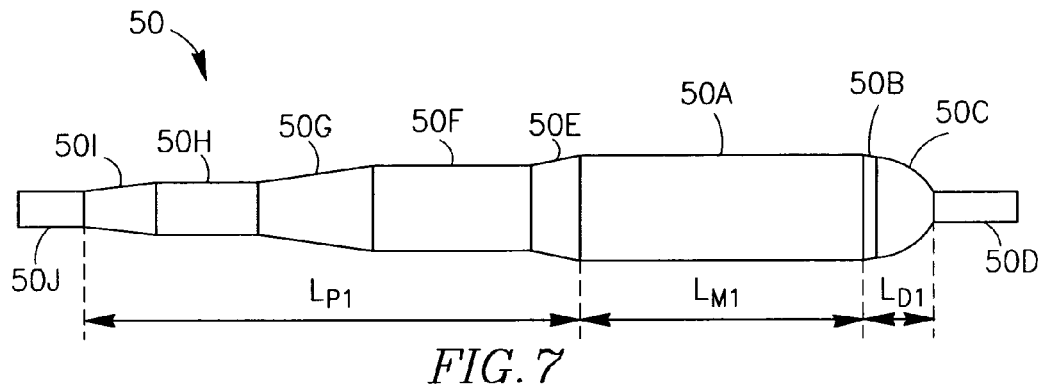
FIGS. 7-10 are schematic side views, illustrating several different embodiments of sleeve-like elements usable in suitable for use in the intussusceptible balloon catheters and catheter systems of the present application.

In FIG. 7, the balloon 50 includes a middle portion 50A, a proximal side portion comprising contiguous portions 50E, 50F, 50G, 50H, 50I and 50J, and a distal side portion comprising contiguous portions 50B, 50C and 50D.

The portions 50A, 50F, 50H 50J and 50D are cylindrical portions. The diameter of the middle portion 50A is larger than the diameters of portions 50F, 50H 50J and 50D. The diameter of portion 50J (which may be attachable to the tip of the outer tube 18 of the catheter system 10 of FIG. 2, if balloon 50 is used instead of the balloon 5) is larger than the diameter of portion 50D (which may be attachable to the tip of the inner tube 17 of the catheter system 10 of FIG. 2, if balloon 50 is used instead of the balloon 5). The portions 50B, 50E, 50G and 50I are frusto-conical portions. Portion 50C is a rounded truncated (truncated dome-like) portion.

The length $L_{P1}$ of the portions 50I, 50H, 50G, 50F and 50E is preferably larger than the length $L_{M1}$ of the portion 50A.

More preferably, the length $L_{P1}$ is larger than $L_{M1}+L_{D1}$ (wherein $L_{D1}$ is the combined length of the portions 50B and 50C.

Figure 8:
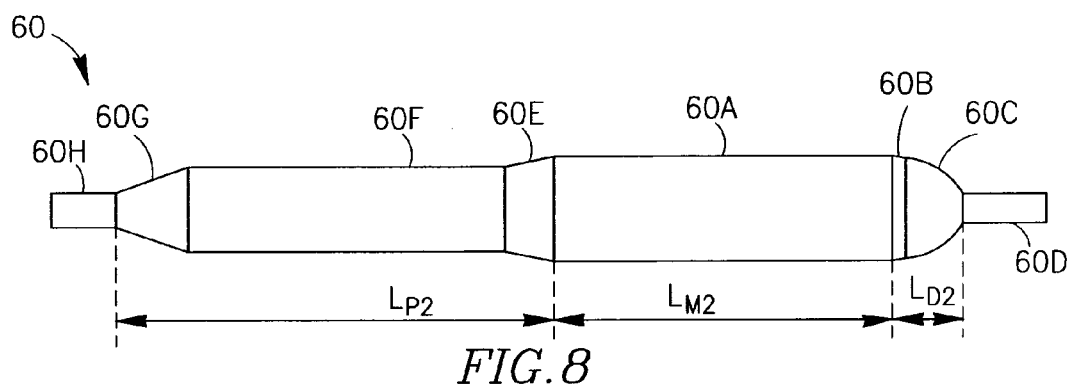

In FIG. 8, the balloon 60 includes a middle portion 60A, a proximal side portion comprising contiguous portions 60E, 60F, 60G and 60H, and a distal side portion comprising contiguous portions 50B, 50C and 50D.

The portions 60A, 60F, 60H and 60D are cylindrical portions. The diameter of the middle portion 60A is larger than the diameters of portions 60A, 60F, 60H and 60D. The diameter of portion 60H (which may be attachable to the tip of the outer tube 18 of the catheter system 10 of FIG. 2, if balloon 60 is used instead of the balloon 5) is larger than the diameter of portion 60D (which may be attachable to the tip of the inner tube 17 of the catheter system 10 of FIG. 2, if balloon 60 is used instead of the balloon 5). The portions 60B, 60G and 60E are frusto-conical portions. Portion 60C is a rounded truncated (truncated dome-like) portion.

The length $L_{P2}$ of the portions 60G, 60F and 60E is preferably larger than the length $L_{M2}$ of the portion 60A.

More preferably, the length $L_{P2}$ is larger than $L_{M2}+L_{D2}$ (wherein $L_{D2}$ is the combined length of the portions 60B and 60C.

Figure 9:
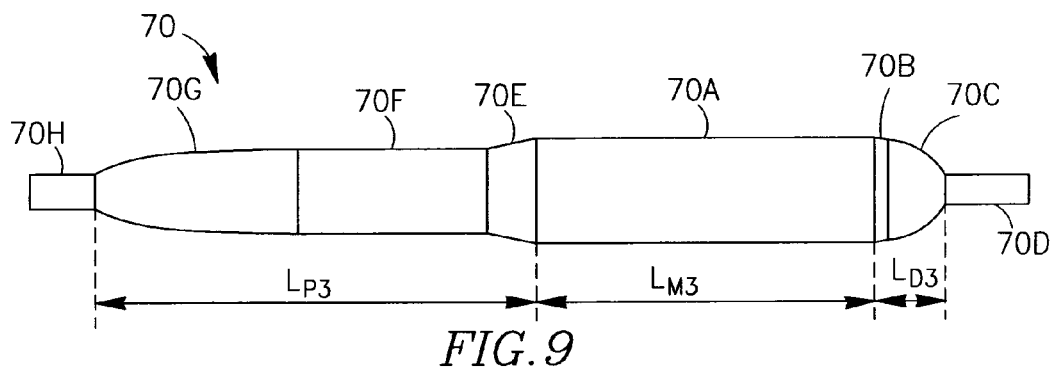

In FIG. 9, the balloon 70 includes a middle portion 70A, a proximal side portion comprising contiguous portions 70E, 70F, 70G and 70H, and a distal side portion comprising contiguous portions 70B, 70C and 70D.

The portions 70A, 70F, 70H and 70D are cylindrical portions. The diameter of the middle portion 70A is larger than the diameters of portions 70A, 70F, 70H and 70D. The diameter of portion 70H (which may be attachable to the tip of the outer tube 18 of the catheter system 10 of FIG. 2, if balloon 70 is used instead of the balloon 5) is larger than the diameter of portion 70D (which may be attachable to the tip of the inner tube 17 of the catheter system 10 of FIG. 2, if balloon 70 is used instead of the balloon 5). The portions 70B and 70E are frusto-conical portions. Portion 70G is a convex tapering portion and portion 70C is a rounded truncated (truncated dome-like) portion.

The length $L_{P3}$ of the portions 70G, 70F and 70E is preferably larger than the length $L_{M3}$ of the portion 70A.

More preferably, the length $L_{P3}$ is larger than $L_{M3}+L_{D3}$ (wherein $L_{D3}$ is the combined length of the portions 70B and 70C.

Figure 10:
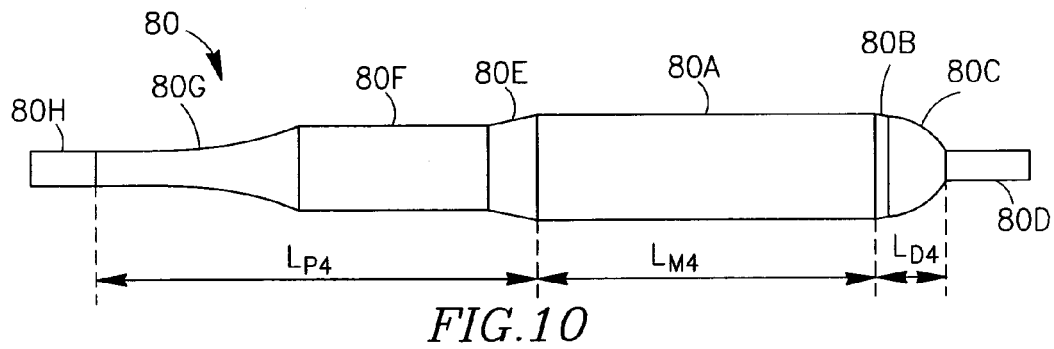

In FIG. 10, the balloon 80 includes a middle portion 80A, a proximal side portion comprising contiguous portions 80E, 80F, 80G and 80H, and a distal side portion comprising contiguous portions 80B, 80C and 80D.

The portions 80A, 80F, 80H and 80D are cylindrical portions. The diameter of the middle portion 80A is larger than the diameters of portions 80A, 80F, 80H and 80D. The diameter of portion 80H (which may be attachable to the tip of the outer tube 18 of the catheter system 10 of FIG. 2, if balloon 80 is used instead of the balloon 5) is larger than the diameter of portion 80D (which may be attachable to the tip of the inner tube 17 of the catheter system 10 of FIG. 2, if balloon 80 is used instead of the balloon 5). The portions 80B and 80E are frusto-conical portions. Portion 80G is a concave tapering portion and portion 80C is a rounded truncated (truncated dome-like) portion.

The length $L_{P4}$ of the portions 80G, 80F and 80E is preferably larger than the length $L_{M4}$ of the portion 80A.

More preferably, the length $L_{P4}$ is larger than $L_{M4}+L_{D4}$ (wherein $L_{D4}$ is the combined length of the portions 80B and 80C.

As may be seen from the above disclosed non-limiting examples, the proximal side of the improved balloons of the present application may comprise any desired combination of portions, including but not limited to, cylindrical, frustoconical, concave tapering, convex tapering, and other desired forms as long as their largest diameters are smaller than the diameter of the middle portion of the expandable balloon.

Additionally, the inflatable distal portion of the balloons of the catheters of the present application may include one or more dome-like portions, truncated dome-like portions, conical portions, frusto-conical portions, corrugated dome-like portions, corrugated conical portions, corrugated frusto-conical portions, corrugated truncated dome-like portions and combinations of the above.

However, preferably, the summed length of all the portions of the proximal side of the balloon (excluding the length of the most proximal portion used for attachment of the proximal side of the balloon to the outer tube 18 of the catheter, such as, for example the portions 5G, 50J, 60H, 70H and 80H of FIGS. 1, 7, 8, 9 and 10, respectively) is equal to or greater than the length of the middle portion of the balloons (such as the middle portions 5A, 50A 60A, 70A and 80A, respectively).

More preferably, the combined length of all the portions of the proximal side portion of the balloon (excluding the length of the most proximal portion used for attachment of the proximal side of the balloon to the outer tube 18 of the catheter, such as, for example the portions 5G, 50J, 60H, 70H and 80H of FIGS. 1, 7, 8, 9 and 10, respectively) is equal to or greater than the sum of the length all the portions of the distal side of the balloon (excluding the length of the most distal portion used for attachment of the distal side of the balloon to the inner tube 17 of the catheter, such as, for example, the portions 5J of FIG. 1 and 50D of FIGS. 7, 8, 9 and 10) and the length of the middle portion of the balloon (such as the middle portions 5A, 50A 60A, 70A and 80A, of FIGS. 1, 7, 8, 9 and 10, respectively).

These length relationships were found to advantageously provide a sufficiently large volume 40 for trapping and containing fluids and/or debris without unnecessarily increasing the length of the balloon (middle) portion which is in contact with blood vessel walls during the period of maximal balloon inflation, while still satisfactorily maintaining a good seal between the blood vessel walls and a portion of the outer surface of the balloon after the completion of intussuscepting of the balloon (as represented in FIG. 5) and before the balloon is inflated.

Figure 11:
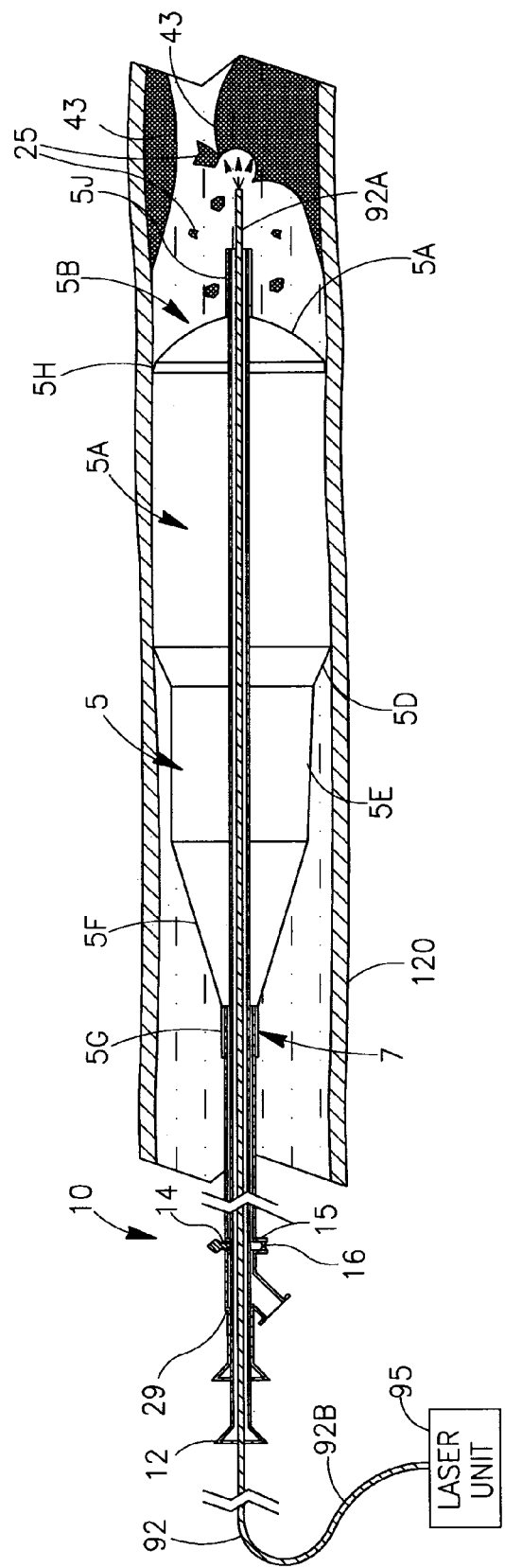
FIG. 11 is a schematic cross sectional diagram illustrating a step of a method of use of the catheter system of the present application for anchoring the catheter against the walls of a blood vessel prior to the insertion of a plaque treating device through a lumen within the catheter.

Reference is now made to FIG. 11 which is a schematic cross sectional diagram illustrating a step of a method of use of the catheter system of the present application for anchoring the catheter against the walls of a blood vessel prior to the insertion of a plaque treating device through a lumen within the catheter.

In FIG. 11 the catheter 10 is shown with the balloon 5 in the fully inflated state in a blood vessel 120. The blood vessel 120 has a plaque region 43 therein. The catheter 10 is inserted into the blood vessel 120 as described hereinabove in detail. The catheter 10 may be inserted over a guide wire as shown in FIG. 2 above or by using any other catheter insertion method known in the art. The catheter 10 is suitably positioned with its distal tip at a suitable position in the vicinity of the plaque 43 and the balloon 5 is fully inflated such that its middle portion 5A firmly anchors the catheter 10 against the walls of the blood vessel 120. If the catheter 10 was guided using a guide wire (not shown), the guide wire is then withdrawn from the lumen of the inner tube 17. A suitable optical fiber 92 is then inserted into the lumen of the inner tube 17 and advanced until the distal tip 92A of the optical fiber 92 is positioned close to or in contact with a portion of the plaque 43. The proximal end 92B of the optical fiber 92 is optically coupled to a laser unit 95 including an Excimer laser, as is known in the art. The plaque 43 may then be treated by excimer laser coronary angioplasty (ELCA) methods, as is known in the art.

Plaque particles resulting from the breakup of the plaque 43 during laser treatment may then be captured and withdrawn from the body of the treated subject by withdrawing the laser fiber 92 from within the lumen of the inner tube 17 and performing the steps for intussuscepting and deflating of the balloon 5 and withdrawing the catheter 10 out of the body of the treated subject, as explained in detail hereinabove and illustrated in FIGS. 4-6 (with respect to the blood vessel 20).

It is noted that while the Example illustrated in FIG. 11 hereinabove relates to plaque treatment using laser ablation methods, the use of the catheter systems disclosed herein is not limited to laser based plaque treating devices and methods but may rather be used in conjunction with many other types of plaque treatment devices and methods. For example, various types of mechanical plaque treating devices known in the art may be inserted into the lumen of the inner tube 17 and used to treat the plaque (43) as is known in the art, followed by withdrawal of the mechanical plaque treating device and performing the balloon intussuscepting, deflating and catheter withdrawal steps disclosed in detail hereinabove, to effect the capture and removal of debris and/or plaque particles and/or fluids and/or secretions from the lumen of the treated blood vessel.

The plaque treating devices which may be inserted into the lumen of the inner tube 17 may include but are not limited to, rotablator burrs, blade like rotatable devices, direction cutting wires and devices, various cutting devices useful for performing directional coronary atherectomy (DCA), devices for performing directional ELCA, devices for performing radio frequency based angioplasty, and/or microwave based angioplasty and/or thermal angioplasty, devices for performing vibrational angioplasty, devices for performing Physiologic low stress angioplasty (PLOSA), or any other device for treating plaque known in the art and insertable through the lumen of the inner tube 17 of the catheter 10 or any other catheters of the present application.

Figure 12:
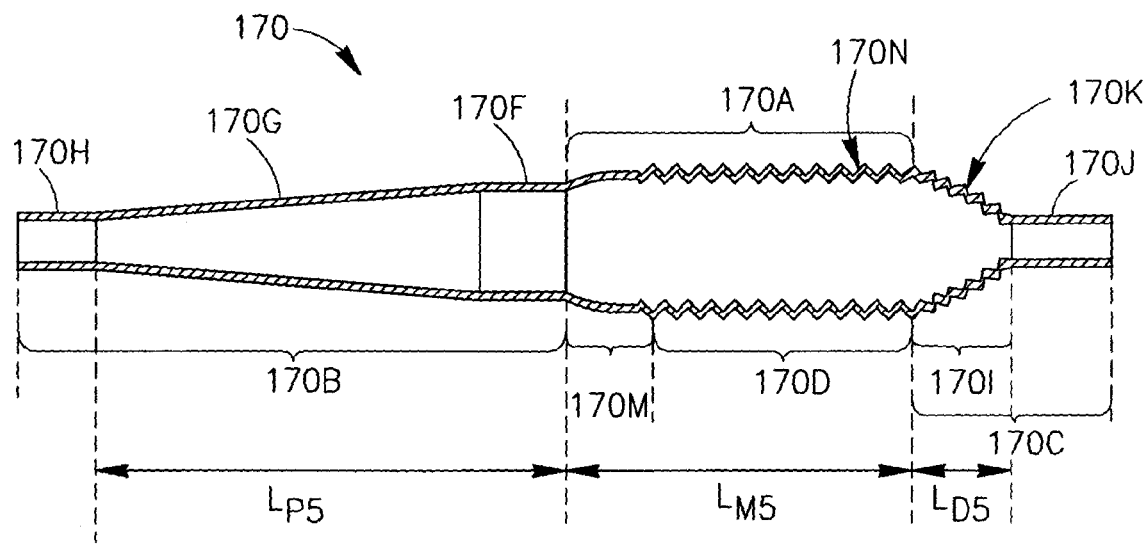
FIGS. 12-13 are schematic cross-sectional diagrams illustrating two different embodiments of corrugated stepped tapering sleeve-like elements suitable for implementing catheters having a corrugated stepped tapering intussusceptible balloons in accordance with additional embodiments of the sleeve-like elements and balloon catheters of the present application.
Figure 13:
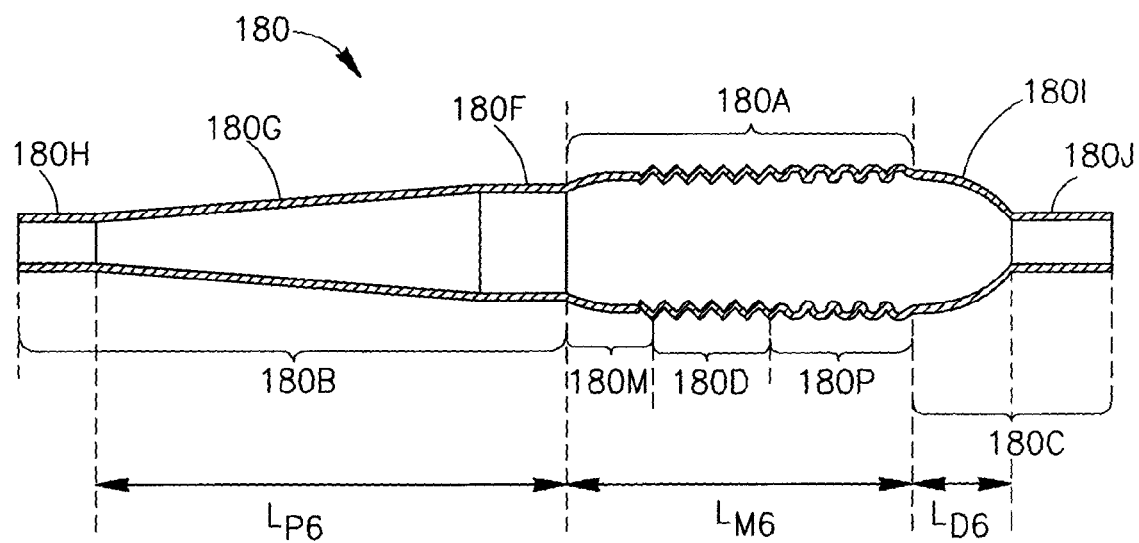

Reference is now made to FIGS. 12-13 which are schematic cross-sectional diagrams illustrating two different embodiments of corrugated stepped tapering sleeve-like elements suitable for implementing catheters having a corrugated stepped tapering intussusceptible balloons in accordance with additional embodiments of the sleeve-like elements and balloon catheters of the present application.

Turning to FIG. 12, the corrugated stepped and tapering sleeve like element 170 includes a middle portion 170A, a corrugated proximal side portion 170B and a distal side portion 170C. The proximal side portion 170B comprises contiguous portions 170H, 170G and 170F. The middle portion 170A comprises contiguous portions 170M and 170D. The portion 170M has a curved (tapering) shape. The tapered portion 170M is not corrugated and the portion 170D is corrugated. The distal side portion 170C comprises a corrugated truncated conical portion 170I (which is contiguous with the corrugated portion 170D of the middle portion 170A) and a non-corrugated cylindrical portion 170J which comprises the distal margin of the balloon 170.

The portions 170H is cylindrical and comprises the proximal margin of the sleeve-like element 170. The sleeve-like element 170 may be used in a catheter similar to the catheter 10 of FIG. 2 by sealingly attaching the portion 170H attached to the outer tube 18 and sealingly attaching the portion 170J to the distal end of the inner tube 17, as described in detail hereinabove for the balloon 5 of FIG. 2.

The portion 170G is a frusto-conical portion. The portion 170F is a cylindrical portion and has (in its inflated state) a diameter larger than the diameter of the portion 170H but smaller than the inflated diameter of the portion 170A. The internal diameter of the cylindrical portion 170I is smaller than the internal diameter of the cylindrical portion 170H. The corrugated structure of the portion 170I may facilitate the folding and intussuscepting of the balloon which is formed when the sleeve-like element 170 is sealingly attached to a catheter. The shape and dimensions of the corrugations 170K of the portion 170I may be similar to the shape and dimensions of the corrugations 170N of the portion 170D. However, this is not obligatory and the shape and dimensions of the corrugations 170K of the portion 170I may be different than the shape and dimensions of the corrugations 170N of the portion 170D.

The length $L_{P5}$ of the portions 170G, 170F is preferably larger than the length $L_{M5}$ of the portion 170A. More preferably, the length $L_{P5}$ is larger than the combined length $L_{M5}+L_{D5}$ (wherein $L_{D5}$ is the length of the portion 170I which is the inflatable part of the distal portion 170C).

Turning to FIG. 13, the corrugated balloon 180 includes a middle portion 180A, a proximal side portion 180B and a distal side portion 180C. The proximal side portion 180B comprises contiguous portions 180H, 180G and 180F similar in shape to the portions 170H, 170G and 170F of FIG. 12, respectively. The distal side portion 180C includes the portions 180I and 180J. The portion 180I is a curved dome-like shaped portion. The portion 180J is cylindrical and comprises the distal margin of the sleeve-like element 180. However, the middle portion 180A comprises a curved tapering portion 180M that is not corrugated, and two contiguous corrugated portions 180D and 180P.

The corrugations of the portion 180D are symmetrical triangular corrugations and the corrugations of the portion 180P are symmetrical rounded or curved corrugations.

The length $L_{P6}$ of the portions 180G, 180F is preferably larger than the length $L_{M6}$ of the middle portion 180A. More preferably, the length $L_{P6}$ is larger than the combined length $L_{M6}+L_{D6}$ (wherein $L_{D6}$ is the length of the portion 180I which is the inflatable part of the distal portion 180C).

It is noted that other embodiments with other mixed types of corrugations are also possible in the balloons (and sleeve-like elements) of the present application. For example, in accordance with an embodiment of the balloons of the present application the middle portion of the balloon may include three contiguous portions (not shown), a first portion with rounded corrugations, a second portion with symmetrical triangular corrugations and a third portion with sawtooth-like corrugations. Thus, many other combinations and sub-combinations of multiple corrugated portions (either contiguous or non-contiguous) with multiple different types of corrugations may be implemented in the balloons and balloon catheters of the present application.

It is noted that while in the embodiments of the balloons (and sleeve-like elements) disclosed hereinabove, the corrugated portion(s) occupied most of the longitudinal dimension of the balloon's middle portion (the portion having the largest diameter of all the balloon portions), this is by no means obligatory. Rather, only a part of the middle portion may be corrugated resulting in a partially corrugated middle portion. Similarly, other embodiments are contemplated in which the middle portion of the balloon is completely non-corrugated while the distal portion of the balloon or a part thereof is corrugated.

It is noted that while the wall thickness of the sleeve-like elements 5, 50, 60, 70, 80 170 and 180 is uniform, this is not obligatory and it is possible to use sleeve-like elements having a non-uniform wall thickness along their length to form balloons having an increased probability of preferential collapse of the distal balloon portion when the balloon is in the inflated state and the inner tube 17 is moved proximally within the outer tube 18.

Figure 14:
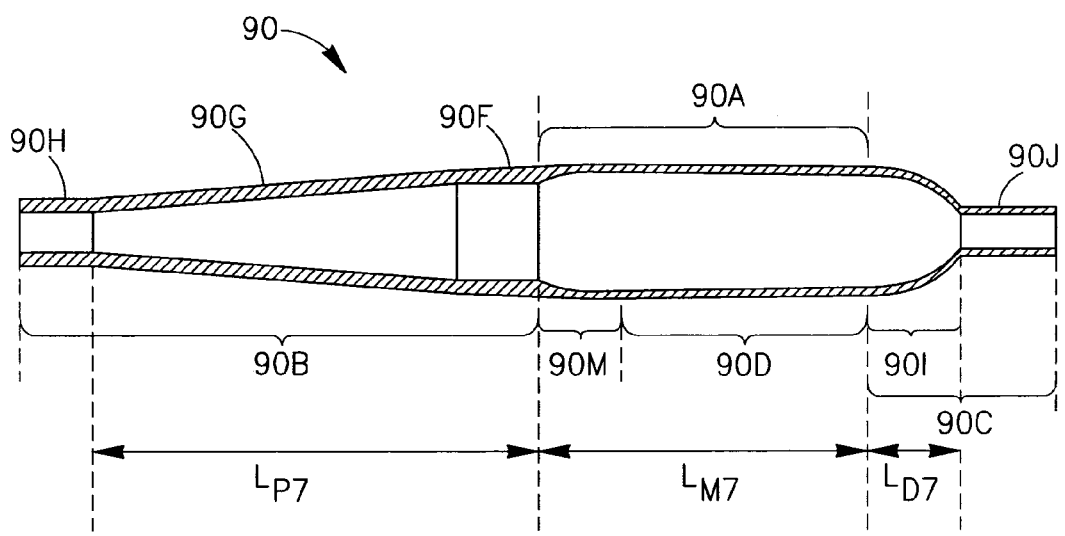
FIG. 14 is a schematic cross-sectional diagram illustrating a corrugated stepped tapering sleeve-like element having a non-uniform wall thickness usable in catheters having a stepped tapering intussusceptible balloon, in accordance with an embodiment of the balloon catheters of the present application.

Reference is now made to FIG. 14 which is a schematic cross-sectional diagram illustrating a corrugated stepped tapering sleeve-like element having a non-uniform wall thickness usable in catheters having a stepped tapering intussusceptible balloon, in accordance with an embodiment of the balloon catheters of the present application.

In FIG. 14, a sleeve-like element 90 includes a cylindrical middle portion 90A, a proximal side portion 90B and a distal side portion 90C. The sleeve-like element 90 has a non-uniform wall thickness along it's length. The proximal side portion 90B comprises contiguous portions 90H, 90G and 90F. The middle portion 90A comprises contiguous portions 90M and 90D. The portion 90M is mechanically reinforced by having a wall thickness increasing therealong in the proximal direction. Therefore, the wall thickness of the portion 90M near the distal end thereof is smaller than the wall thickness of the portion 90M near the proximal end thereof. This reinforcing advantageously increases the resistance to collapsing of the proximal portion side of the balloon 90 when the inner tube 17 of the catheter (not shown in FIG. 14 for the sake of clarity of illustration) is pulled proximally. The portion 90D is a cylindrical portion having a uniform wall thickness equal to the wall thickness at the distal side of the portion 90M. The distal side portion 90C comprises a truncated dome-like portion 90I which is contiguous with the cylindrical portion 90D, and a cylindrical portion 90J. The wall thickness of the proximal portion 90B is uniform. The wall thickness of the proximal portion 90B is equal to the wall thickness at the proximal (and thicker) end of the portion 90M.

The wall thickness of the dome-like portion 90I of the distal portion 90C is also non-uniform. The wall thickness at the proximal end of the portion 90I is equal to the wall thickness of the portion 90D and gradually thins in the distal direction such that the wall thickness at the distal end of the portion 90I is smaller than the wall thickness at the proximal end of the portion 90I.

The thin wall thickness at the distal end of the distal portion 90I further increases the probability for beginning of collapse of the distal portion 90I of the balloon 90 when the inner tube 17 is pulled proximally within the outer tube 18. This combines with the reduced probability of the folding of the proximal side of the balloon 90 due to the reinforcing of the portion 90M to ensures that when the sleeve-like element 90 is attached to a catheter and a pulling force is applies by the distal tip of the inner tube 17 to the distal portion of the balloon 90 by moving the inner tube 17 of the catheter in the proximal direction, as disclosed hereinabove, the distal side of the balloon 90 will fold (by collapsing) at a lower force than the force required to cause folding of the balloon at the thicker walled region of the proximal side portion 90B and the portion 90M.

The length $L_{P7}$ of the portions 90G, 90F is preferably larger than the length $L_{M7}$ of the middle portion 90A. More preferably, the length $L_{P7}$ is larger than the combined length $L_{M7}+L_{D7}$ (wherein $L_{D7}$ is the length of the portion 90I which is the inflatable part of the distal portion 90C).

It will be appreciated by those skilled in the art that the balloons of the present application are not limited to the particular examples disclosed and illustrated and that various combinations of balloon features may be used such as but not limited to, tapered stepped balloons with non-uniform wall thickness and at least one corrugated portion (such as a fully or partially corrugated inflatable middle portion, and/or a fully or partially corrugated inflatable distal portion and the like).

Similarly, in balloons having a corrugated part, any type and shape of corrugations (including, but not limited to, triangular corrugations, rounded corrugations, sawtooth-like corrugations, longitudinally symmetrical corrugations, longitudinally non-symmetrical corrugations, and any combinations of corrugation types) may be used in implementing the tapered balloons of the present application.

Furthermore, in balloons having non-uniform wall thickness, any type of longitudinal wall thickness profile may be used that advantageously assists the reduction of the probability of collapse of the balloons proximal side. Thus, other balloon parts may be reinforced which are different than the reinforced balloon parts illustrated in FIG. 14.

Typically, in the reinforced balloons and sleeve-like elements of the present application, the ratio of the wall thickness of the thinnest part of the balloon wall to the wall thickness of the thickest part of the balloon may be in the range of 0.2-0.5. However, other ratios below or above this range may also be used depending, inter alia, on the balloon dimensions, the material used for making the balloon, the balloon's nominal inflation pressure, and other mechanical and design considerations.

Figure 15:
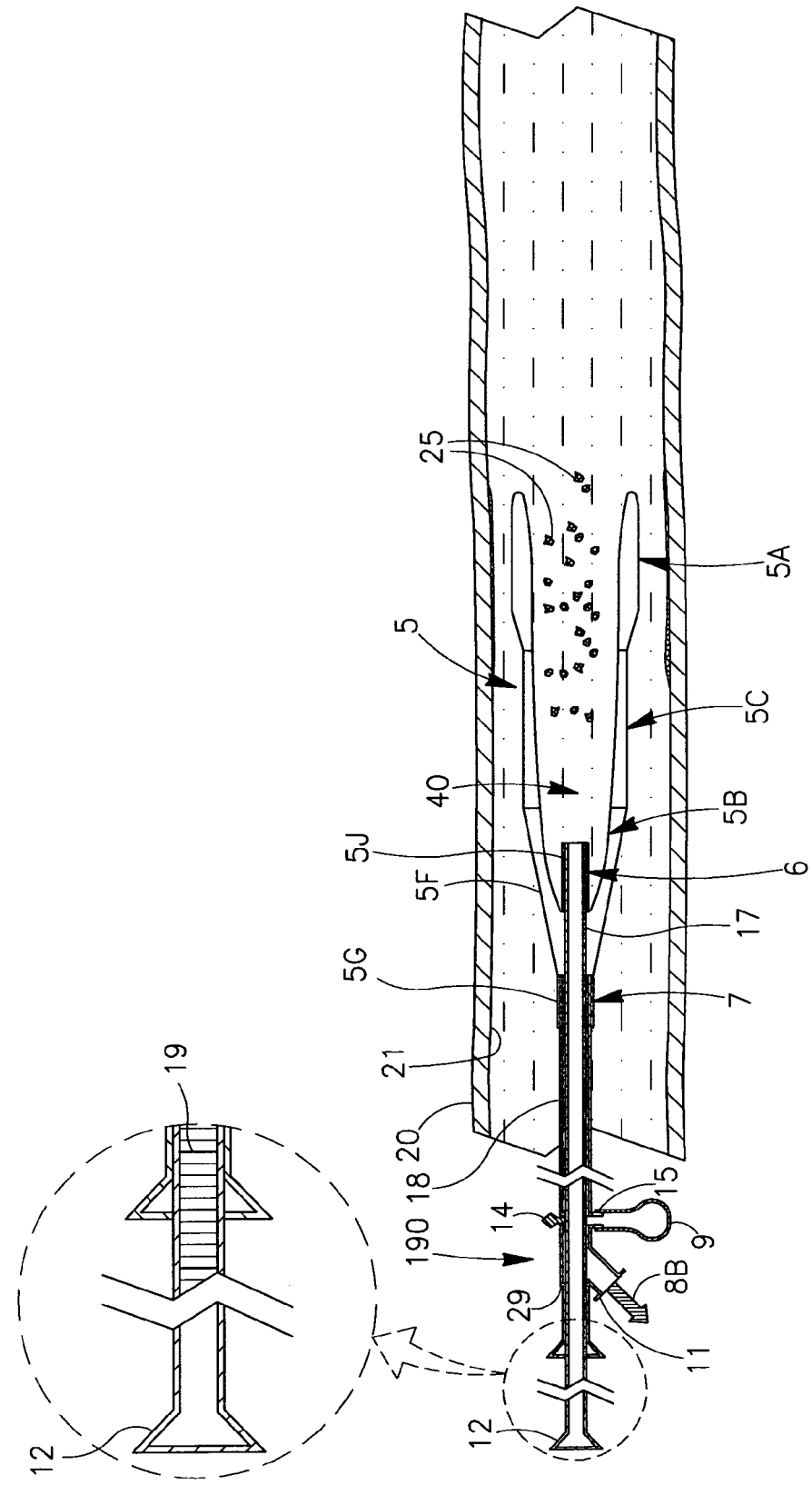
FIG. 15 is a schematic cross-sectional diagram illustrating a catheter system including the intussusceptible inflatable balloon of FIG. 4 and including a compliant member usable as a pressure adjusting mechanism in accordance with another embodiment of the catheter systems of the present application.

FIG. 15 is a schematic cross-sectional diagram illustrating a catheter system including the intussusceptible inflatable balloon of FIG. 4 and including a compliant member usable as a pressure adjusting mechanism in accordance with another embodiment of the catheter systems of the present application.

The balloon catheter 190 of FIG. 15 is similar in construction and operation to the catheter 10 of FIG. 6 except that the over-pressure valve 16 of FIG. 6 is eliminated and is replaced by a compliant member 9 such as (but not limited to) an inflatable and expandable balloon made from latex or from any other suitable expandable material. The compliant member 9 is sealingly attached to the outlet 15 to seal the outlet 15. In this embodiment, the outlet 15 is in fluidic communication with the lumen of the inflatable balloon 5. When the balloon 5 of the catheter 190 is intussuscepted while it is in the inflated state (by pulling the inner tube 17 proximally), the compliant member 9 may expand to accommodate some of the inflating fluid expelled from the lumen of the balloon 5, relieving some of the over-pressure in the lumen of the balloon 5.

Moreover, in accordance with yet another embodiment of the catheters of the present application, the outer tube 18, or portions thereof, may be made inflatable or expandable or compliant, such that over-pressure conditions may be at least partially resolved by the expansion of the tube 18 or of a compliant portion thereof.

It is noted, however, that in embodiments of the catheters having no over-pressure valve outlet 15 and no over-pressure valve 16 and no other pressure adjusting mechanism, the balloon 5 may have a substantially increased in the pressure therewithin during the period in which it is intussuscepted while the fluid port 11 is sealed.

It will be appreciated that the improved balloons of the catheters and catheter systems disclosed in the present application may also be used for delivering, positioning and expanding any suitable type of stent or stents as is known in the art of balloon mediated stent deployment.

It is noted that while most of the examples disclosed herein illustrate catheters and catheter systems particularly suitable to treating plaque in blood vessels this is not intended to limit the scope of the balloons catheters and systems to treatment of blood vessels. Rather, the balloons, catheters and systems disclosed in the present application may be used for performing various different types of treatment within bodily passages different than blood vessels and for capturing and removing solid and/or fluid materials and/or particles from within such bodily passages and withdrawing such removed materials outside the body of the treated subject.

The invention claimed is:

1. A balloon catheter comprising:
an outer conduit;
an inner conduit, suitable for passage over a guide wire, disposed within the lumen of said outer conduit such that the longitudinal axes of said inner and outer conduits are substantially parallel, and positioned such that the distal tip of said inner conduit extends beyond the distal tip of said outer conduit, said inner conduit is capable of being moved along its longitudinal axis in relation to said outer conduit;
an inflatable balloon having a proximal margin attached to the outer surface of the distal tip of said outer conduit, and a distal margin attached to the outer surface of the portion of the inner conduit that extends beyond the distal tip of said outer conduit, said inflatable balloon includes a cylindrical middle portion, a distal side portion having at least one tapering part and a proximal side portion having at least one tapering part, wherein the length of said inflatable proximal side portion is equal to or larger than the length of said middle portion, said proximal portion comprises at least a second cylindrical portion having in the inflated state a diameter smaller than the diameter of said middle portion in the inflated state, said proximal portion also comprises at least two frusto-conical portions flanking the distal and the proximal sides of said second cylindrical portion, and wherein the distal end portion of said balloon is capable of intussuscepting upon proximal movement of said inner conduit in relation to said outer conduit; and a fluid port for introducing an inflation fluid into the space formed between the inner surface of said outer conduit and the outer surface of said inner conduit and into the lumen of said balloon, and for removing said fluid from said space and from said lumen.

2. The balloon catheter according to claim 1, wherein said proximal portion also comprises one or more portions selected from, cylindrical portions, frusto-conical portions, concave tapering portions, convex tapering portions, and combinations thereof.

3. The balloon catheter according to claim 1 wherein the length of said proximal side portion is equal to or larger than the combined length of said middle portion and said inflatable distal portion.

4. The balloon catheter according to claim 1 wherein at least part of said inflatable balloon is a corrugated part.

5. The balloon catheter according to claim 4 wherein said corrugated part is selected from,
at least part of said distal portion of said balloon,
at least part of said middle portion of said balloon, and
at least part of said distal portion and said middle portion of said balloon.

6. The balloon catheter according to claim 1 wherein said balloon has a non-uniform wall thickness along its longitudinal axis.

7. The balloon catheter according to claim 6 wherein the wall thickness of at least part of said distal portion is smaller than the wall thickness of at least part of said middle portion of said balloon.

8. The balloon catheter according to claim 6 wherein the wall thickness of at least part of said distal portion is smaller than the wall thickness of at least part of said inflatable proximal portion of said balloon.

9. The balloon catheter according to claim 6 wherein the wall thickness of at least part of said distal portion is smaller than the wall thickness of at least part of said middle portion of said balloon.

10. The balloon catheter according to claim 1, wherein said distal portion of said inflatable balloon comprises one or more portions selected from dome-like portions, truncated dome-like portions, conical portions, frusto-conical portions, corrugated dome-like portions, corrugated conical portions, corrugated frusto-conical portions, corrugated truncated dome-like portions and combinations thereof.

11. The balloon catheter according to claim 1, wherein said balloon catheter also includes a pressure adjusting mechanism for preventing substantial pressure changes within said space and the lumen of said balloon upon axial movement of said inner conduit in relation to said outer conduit.

12. The balloon catheter according to claim 11, wherein said pressure adjusting mechanism is selected from,
a pressure adjusting mechanism comprising a syringe-like structure disposed at the proximal end of said balloon catheter, said syringe-like structure includes a barrel and a plunger disposed within said barrel, said plunger co-axially surrounds the proximal end of the inner conduit, and is affixed thereto,
an outlet in fluidic communication with the lumen of said inflatable balloon and having an opening and a compliant member sealingly attached to said opening for at least partially relieving over-pressure in said lumen,
an over-pressure valve outlet in fluidic communication with the lumen of said inflatable balloon and an over-pressure valve disposed within said over-pressure outlet to allow discharging of fluid from said lumen when over-pressure conditions develop in said lumen, and
an expandable or inflatable portion of said outer conduit, capable of being inflated when over-pressure conditions occur in the lumen of said balloon to at least partially relieve the over-pressure in said lumen.

13. A stepped tapered element for use in constructing the catheter of claim 1, the element comprises:
a sleeve-like element including a first cylindrical middle portion, a distal side portion having at least one tapering part and a proximal side portion having at least one tapering part, wherein the length of said proximal side portion is equal to or larger than the length of said middle portion, said proximal portion comprises at least a second cylindrical portion having in the inflated state a diameter smaller than the diameter of said first cylindrical middle portion in the inflated state, said proximal portion also comprises at least two frusto-conical portions flanking the distal and the proximal sides of said second cylindrical portion, said proximal side portion has a first open end with a first diameter, said distal side portion has a second open end with a second diameter smaller than said first diameter, wherein the length of said proximal side portion is equal to or larger than the length of said middle portion.

14. The sleeve-like element according to claim 13, wherein said proximal portion also comprises one or more portions selected from, cylindrical portions, frusto-conical portions, concave tapering portions, convex tapering portions, and combinations thereof.

15. The sleeve-like element according to claim 13 wherein the length of said proximal side portion is equal to or larger than the combined length of said middle portion and said distal portion.

16. The sleeve-like element according to claim 13 wherein at least part of said element is a corrugated part.

17. The sleeve-like element according to claim 16 wherein said corrugated part is selected from,
at least part of said distal portion of said element,
at least part of said middle portion of said element, and
at least part of said distal portion and said middle portion of said element.

18. The sleeve-like element according to claim 13 wherein said element has a non-uniform wall thickness along its longitudinal axis.

19. The sleeve-like element according to claim 18 wherein the wall thickness of at least part of said distal portion is smaller than the wall thickness of at least part of said middle portion of said element.

20. The sleeve-like element according to claim 18 wherein the wall thickness of at least part of said distal portion is smaller than the wall thickness of at least part of said proximal portion of said element.

21. The sleeve-like element according to claim 18 wherein the wall thickness of at least part of said distal portion is smaller than the wall thickness of at least part of said middle portion of said element.

22. The sleeve-like element according to claim 13, wherein said distal portion of said element comprises one or more portions selected from dome-like portions, truncated dome-like portions, conical portions, frusto-conical portions, corrugated dome-like portions, corrugated conical portions, corrugated frusto-conical portions, corrugated truncated dome-like portions and combinations thereof.

23. The sleeve-like element according to claim 13, wherein the shape of said distal side portion of said sleeve-like element is selected from a dome-like shape, a truncated dome-like shape, a conical shape, a frusto-conical shape, a corrugated dome-like shape, a corrugated conical shape and a corrugated frusto-conical shape, and a corrugated truncated dome-like shape.

24. A method for collecting debris from an internal passage of a mammalian subject comprising the steps of:
- inserting a balloon catheter comprising a balloon as defined in claim 1 into said internal passage, and advancing said catheter until the distal tip thereof has reached the site, at which it is desired to collect debris;
- inflating said balloon with expansion fluid;
- pulling the inner conduit of said balloon catheter in a proximal direction, for collapsing the distal end of said balloon to form a cavity within said balloon into which debris is collected and entrapped;
- deflating the intussuscepted balloon; and
- removing the deflated balloon catheter from the internal passage of the subject, together with the entrapped debris.

25. The method according to claim 24, wherein the internal passage is a blood vessel.

26. The method according to claim 24, wherein said step of pulling comprises pulling the inner conduit of said balloon catheter in a proximal direction to form said cavity, such that all of the surface portions of said middle portion are internally disposed within said cavity to enhance retention of said debris.

27. The method according to claim 24, wherein said catheter includes a mechanism for preventing substantial pressure changes when said inner conduit is moved proximally within said outer conduit while said balloon is inflated and said fluid port is closed, and wherein said step of pulling comprises pulling said inner conduit of said balloon catheter in a proximal direction for collapsing the distal end of said balloon to form a cavity within said balloon into which said debris is collected and entrapped without causing substantial pressure changes within the lumen of said balloon during said step of pulling.

* * * * *